US010238329B2

(12) United States Patent
Bansal et al.

(10) Patent No.: US 10,238,329 B2
(45) Date of Patent: Mar. 26, 2019

(54) APPARATUS, METHOD AND COMPUTER-ACCESSIBLE MEDIUM FOR DIAGNOSING AND SUBTYPING PSYCHIATRIC DISEASES

(75) Inventors: Ravi Bansal, Cranbury, NJ (US); Bradley S. Peterson, Somers, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 552 days.

(21) Appl. No.: 13/994,925

(22) PCT Filed: Dec. 16, 2011

(86) PCT No.: PCT/US2011/065419
§ 371 (c)(1),
(2), (4) Date: Feb. 20, 2014

(87) PCT Pub. No.: WO2012/083136
PCT Pub. Date: Jun. 21, 2012

(65) Prior Publication Data
US 2014/0155730 A1    Jun. 5, 2014

Related U.S. Application Data

(60) Provisional application No. 61/424,172, filed on Dec. 17, 2010, provisional application No. 61/469,912, filed on Mar. 31, 2011.

(51) Int. Cl.
*A61B 5/00* (2006.01)
*A61B 5/0476* (2006.01)
(Continued)

(52) U.S. Cl.
CPC .......... *A61B 5/4064* (2013.01); *A61B 5/0042* (2013.01); *A61B 5/04008* (2013.01);
(Continued)

(58) Field of Classification Search
CPC .......... A61B 6/037; A61B 5/7264; A61B 5/05; A61B 5/16; A61B 5/04005; A61B 5/055;
(Continued)

(56) References Cited

U.S. PATENT DOCUMENTS

7,840,247 B2    11/2010  Liew et al.
2008/0101665 A1   5/2008  Collins et al.
(Continued)

FOREIGN PATENT DOCUMENTS

WO    WO 2009/146388    12/2009

OTHER PUBLICATIONS

Fernández, Alberto, et al. "Complexity analysis of spontaneous brain activity in attention-deficit/hyperactivity disorder: diagnostic implications.". Biological psychiatry 65.7 (2009): 571-577.*
(Continued)

*Primary Examiner* — Carolyn Pehlke
(74) *Attorney, Agent, or Firm* — Hunton Andrews Kurth LLP

(57) ABSTRACT

Exemplary method, system and computer-accessible medium can be provided for diagnosing at least one disease and/or a subtype within a disease. For example, it is possible to determine at least one region of interest, and obtain a plurality of data points associated with each of such region(s) of interest. It is also possible to identify a particular pattern of the data points across each of such region(s) of interest. Further, it is possible, e.g., using a computer arrangement, to determine a likelihood of the disease(s) and/or the subtype by comparing the particular pattern to at least one known pattern.

43 Claims, 10 Drawing Sheets

(51) Int. Cl.
| | |
|---|---|
| *A61B 5/16* | (2006.01) |
| *A61B 6/00* | (2006.01) |
| *A61B 6/03* | (2006.01) |
| *A61B 5/04* | (2006.01) |
| *A61B 8/08* | (2006.01) |
| *G01V 3/14* | (2006.01) |
| *A61B 5/055* | (2006.01) |

(52) U.S. Cl.
CPC ............ *A61B 5/0476* (2013.01); *A61B 5/055* (2013.01); *A61B 5/165* (2013.01); *A61B 5/168* (2013.01); *A61B 5/4082* (2013.01); *A61B 5/726* (2013.01); *A61B 5/7282* (2013.01); *A61B 5/742* (2013.01); *A61B 6/032* (2013.01); *A61B 6/501* (2013.01); *A61B 6/5217* (2013.01); *A61B 8/0808* (2013.01); *G01V 3/14* (2013.01); *G06K 2209/05* (2013.01)

(58) Field of Classification Search
CPC ......... A61B 5/0476; A61B 8/00; A61B 5/726; A61B 5/4064; A61B 5/4076; G06T 7/0012
USPC .......... 600/407–410, 436, 437; 382/128–132
See application file for complete search history.

(56) References Cited

U.S. PATENT DOCUMENTS

2009/0220429 A1   9/2009   Johnsen et al.
2010/0316283 A1   12/2010  Greer

OTHER PUBLICATIONS

Chang, Wei-Tang, et al. "Spatially sparse source cluster modeling by compressive neuromagnetic tomography." NeuroImage 53.1 (2010): 146-160.*
Abdelnour, F., B. Schmidt, and T. J. Huppert. "Topographic localization of brain activation in diffuse optical imaging using spherical wavelets." Physics in medicine and biology 54.20 (2009): 6383.*
Yao, Zhijian, et al. "Regional homogeneity in depression and its relationship with separate depressive symptom clusters: a resting-state fMRI study." Journal of affective disorders 115.3 (2009): 430-438.*
Chun-Lin, Liu. "A tutorial of the wavelet transform." NTUEE, Taiwan (2010).*
Bernal-Rusiel, Jorge L., Mercedes Atienza, and Jose L. Cantero. "Detection of focal changes in human cortical thickness: spherical wavelets versus gaussian smoothing." NeuroImage 41, No. 4 (2008): 1278-1292.*
Angenent, Sigurd, Steven Haker, Allen Tannenbaum, and Ron Kikinis. "Conformal geometry and brain flattening." In Medical Image Computing and Computer-Assisted Intervention—MICCAI'99, pp. 271-278. Springer Berlin/Heidelberg, 1999.*
Resnick, Susan M., Alberto F. Goldszal, Christos Davatzikos, Stephanie Golski, Michael A. Kraut, E. Jeffrey Metter, R. Nick Bryan, and Alan B. Zonderman. "One-year age changes in MRI brain volumes in older adults." Cerebral cortex 10, No. 5 (2000): 464-472.*
Mohamed, Ashraf, and Christos Davatzikos. "Morphometric Analysis of Normal and Pathologic Brain Structure Via High-Dimensional Shape Transformations." Deformable Models (2007): 393-445.*
Angenent S, et al "On the Laplace-Beltrami operator and brain surface flattening." IEEE Transactions on Medical Imaging. 1999;18(8):700-11.
Ashburner J, Friston KJ. "Voxel-based morphometry—The Methods." NeuroImage. 2000;11(6):805-821.
Bansal R, et al "ROC-based assessments of 3D cortical surface-matching algorithms." Neuroimage. 2005;24:150-62.
Blumberg HP, et al. "Amygdala and hippocampal volumes In adolescents and adults with Bipolar Disorder". Arch Gen Psychiatry. 2003;60:1201-1208.
Blumberg HP, et al. "A Functional Magnetic Resonance Imaging Study of bipolar disorder. State- and . . . prefrontal cortices." Arch Gen Psychiatry. 2003;60:601-609.
Blumberg HP et al. "Age, Rapid-Cycling, & Pharmacotherapy Effects on Ventral Prefrontal Cortex in Bipolar Disorder: A Cross-Sectional Study" Bio Psychiatry. 2006;59(7):611-8.
Conners CK, et al "The revised Conners' Parent Rating Scale (CPRS-R): factor structure, reliability, and criterion validity." J Abnorm Child Psychol. 1998;26:257-268.
Conners CK et al "Revision & restandardization of the Conners Teacher Rating Scale (CTRS-R): factor structure . . . validity." J Abnorm Child Psychol. 1998;26:279-291.
Csernansky JG, et al. "Abnormalities of thalamic volume and shape in schizophrenia." Am J Psychiatry. 2004;161:896-902.
Davatzikos C, et al. Detection of prodromal Alzheimer's disease via pattern classification of MRI. Neurobiol Aging. 2008;29(4):514-523.
Davatzikos C, et al. "Whole-brain morphometric study of schizophrenia revealing a spatially complex set of focal abnormalities." Arch General Psychiatry. 2005;62:1218-1227.
Duchesnay E, et al. "Classification Based on Cortical Folding Patterns." IEEE Trans on Medical Imaging. 2007;26(4):553-565.
Duda RO, et al. "Pattern Classification and Scene Analysis: 2nd Edition Part 1: Pattern Classification" John Wiley & Sons; 1973.
Endicott J and Spitzer RL. "A diagnostic interview: the Schedule for Affective Disorders and Schizophrenia." Arch Gen Psychiatry. 1978;35:837-844.
Peterson BS. "Form Determines Function: New Methods for Identifying the . . . Childhood Disorders." J of the Am Academy of Child and Adolescent Psychiatry. 2010;49(6):533-538.
Fan Y, et al. "Classification of structural images via high-dimensional image warping, robust feature extraction, & {SVM}." Classification of Structural Images. 2005;8:1-8.
Haubold A, et al "Progress in Using Brain Morphometry as a Clinical Tool for Diagnosing Psychiatric Disorders." J Child Psychol Psychiatry, May 2012 ; 53(5): 519-535.
Herholz K, et al "Discrimination between Alzheimer dementia and controls by automated analysis of multicenter FDG PET." Neuroimage. 2002;17:302-316.
Holgersson M. "The limited value of cophenetic correlation as a clustering criterion" Pattern Recognition. 1979;10(4):287-295.
Rohlf FJ. "Adaptive hierarchical clustering schemes." Systematic Zoology 1970;19:58-82.
Insel T, et al. "Research Domain Criteria (RDoC): Toward a New Classification Framework for Research on Mental Disorders." Am J Psychiatry. 2010;167(7):748-751.
Jack CR, et al. "Comparison of different MRI brain atrophy rate measures with clinical disease progression in AD." Neurology. 2004;62:591-600.
Kaufman J, et al. "Schedule for Affective Disorders . . . Version (K-SADS-PL): initial reliability & validity data." J Am Acad Child Adolesc. Psychiatry. 1997; 36:980-988.
Kawasaki Y, et al. "Multivariate voxel-based morphometry successfully differentiates schizophrenia patients from healthy controls." Neuroimage. 2007;34:235-42.
Kloppel S, et al. "Automatic Classification of MR Scans in Alzheimer's Disease." Brain. 2008;131(3):681-689.
Lao Z, et al. "Morphological classification of brains via high dimensional shape transformations and machine learning methods." Neuroimage. 2004;21:46-57.
Leckman JF, et al. "Best estimate of lifetime psychiatric diagnosis: a methodological study." Arch Gen Psychiatry. 1982;39:879-83.
Lerch JP, et al. "Automated cortical thickness measurements from MRI can . . . separate Alzheimer's patients from normal elderly controls." Neurobiol Aging. 2006;29(1): 23-30.
Teipel SJ, et al. "Multivariate deformation-based analysis of brain atrophy to predict Alzheimer's disease in mild cognitive impairment." NeuroImage. 2007;38(1):13-24.

(56) References Cited

OTHER PUBLICATIONS

Lochhead RA, et al. "Regional brain gray matter volume differences . . . disorder as assessed by optimized voxel-based morphometry." Bioi Psychiatry. 2004;55(12):1154-1162.
Luders E, et al. "Mapping cortical gray matter in the young adult brain: Effects of gender." NeuroImage. 2005;26(2):493-501.
Mourao-Miranda J, et al. "Classifying brain . . . The discriminating activation patterns: Support Vector Machine on functional MRI data." Neuroimage. 2005;28:980-95.
Ou Y and Davatzikos C. "DRAMMS: deformable registration via attribute matching and mutual-saliency weighting." Info Processing Medical Imaging. 2009;21:50-62.
Peterson BS, et al. "Morphology features of the Amygdala and Hippocampus in Children and Adults with Tourette Syndrome FREE." Arch General Psychiatry. 2007:6411:1281-1291.
Peterson BS, et al. "Cortical thinning in persons at increased familial risk for major depression." Proc Natl Acad Sci USA. 2009;106:6273-6278.
Leckman JF, et al. "The Yale Global Tic Severity Scale: initial testing of a clinician-rated scale of tic severity." J Am Acad Child Adolesc Psychiatry. 1989;28:566-573.
Toga AW and Thompson PA. "Mapping brain asymmetry." Nature Neuroscience. 2003;4(1):37-48.
Grados JJ and Russo-Garcia KA. "Comparison of the Kaufman Brief Intelligence . . . economically disadvantaged African American youth." J Clin Psychol. 1999;55(9):1063-1071.
Goodman WK, et al. "The Yale-Brown Obsessive Compulsive Scale, I: development, use, and reliability." Arch Gen Psychiatry. 1989;46:1006-1011.
Scahill L, et al. "Children's Yale-Brown Obsessive Compulsive Scale: reliability and validity." J Am Acad Child Adolesc Psychiatry. 1997;36:844-852.
DuPaul GJ. "Parent and teacher ratings of ADHD symptoms: psychometric properties in a community-based sample." J Clin Child Psychol. 1991;20:245-253.
Wexler BE, et al. "Neuropsychological Near Normality and Brain Structure Abnormality in Schizophrenia." Am J Psychiatry. 2009;166:189-195.
Kay SR, et al. "The Positive and Negative Symptom Scale (PANSS) for Schizophrenia." Schizophrenia Bulletin. 1987;13:261-76.
Weissman MM, et al. "Families at High and Low Risk for Depression." Arch Gen Psychiatry. 2005;62:29-36.
Peterson BS, et al. "Reduced basal ganglia volumes in tourette's syndrome using three-dimensional . . . techniques from magnetic resonance images." Neurology. 1993;43(5):941-949.
Kates WR, et al. "Reliability and validity of MRI measurement of the amygdala and hippocampus in children with fragile X syndrome." Psychiatry Res. Neuroimaging 1997;75:31-48.

Watson C, et al. "Anatomic basis of amygdaloid and hippocampal volume measurement by magnetic resonance imaging." Neurology. 1992;42(9):1743-1750.
Sled GJ, et al "A Nonparametric Method for Automatic Correction of Intensity Nonuniformity in MRI Data I." IEEE Trans of Medical Imaging. 1998;17(1):87-97.
Shattuck DW, Leahy RM. "BrainSuite: An Automated Cortical Surface Identification Tool." Medical Image Analysis. 2002;8(2):129-42).
Viola P, "Alignment by Maximization of Mutual Information." IEEE Proc of the 5th Int Conf on Computer Vision; Jun. 20-23, 1995; Boston, MA.
Christensen GE, et al. "3D brain mapping using a deformable neuroanatomy." Physics in medicine and biology. 1994;39(3):609-618.
Lorensen W. and Cline H. "Marching Cubes: a High-Resolution 3D surface construction algorithm." Computer Graphics. 1987;21:163-169.
Cohen A, et al. "Multiresolution analysis, wavelets and fast algorithms on an interval." CR Acad Sci Paris Ser I Math I. 1993;316:417-21.
Schroder P, et al. Efficiently Representing Function on the Sphere. Proceedings of the 22nd annual conference on Computer graphics and interactive techniques 1995:161-72.
Sweldens W. The lifting scheme: A custom design construction of biorthogonal wavelets. Dept of Math, University of South Carolina, 1994 Contract No. Tech. Rep. 1994:7.
International Search Report for International Patent Application No. PCT/US2011/065419 dated Apr. 19, 2012.
International Written Opinion for International Patent Application No. PCT/US2011/065419 dated Apr. 19, 2012.
First, Michael B. et al., "Structured Clinical Interview for DSM-IV Axis I Disorders," SCID-I Clinician Version ScoreSheet, Biometrics Research Department, New York State Psychiatric Institute, American Psychiatric Press, Inc., pp. 1-67, 1997.
First, Michael B. et al., "User's Guide for the Structured Clinical Interview for DSM-IV Axis I Disorders," SCID-I Clinician Version, Biometrics Research Department, New York State Psychiatric Institute, American Psychiatric Press, Inc., pp. 1-139, 1997.
First, Michael B. et al., "User's Guide for the Structured Clinical Interview for DSM-IV Axis II Personality Disorders," SCID-II, Biometrics Research Department, New York State Psychiatric Institute, American Psychiatric Press, Inc., pp. 1-98, 1997.
"WAIS-III; WMS-III, Technical Manual," The Psychological Corporation, Harcourt Brace & Company, pp. 1-168, 1997.
Wechsler, David, "WISC-III, Manual," The Psychological Corporation, Harcourt Brace Jovanovich, Inc. pp. 1-311, 1991.

\* cited by examiner

APPARATUS, METHOD AND COMPUTER-ACCESSIBLE MEDIUM FOR DIAGNOSING AND SUBTYPING PSYCHIATRIC DISEASES

CROSS-REFERENCE TO PRIOR APPLICATION(S)

This application relates to and claims the benefit of priority to International Patent Application No. PCT/US11/065419 filed on Dec. 16, 2011, and claims priority to U.S. Provisional Application Ser. No. 61/424,172 filed on Dec. 17, 2010 and U.S. Provisional Application Ser. No. 61/469,912, filed on Mar. 31, 2011, both of which are incorporated by reference herein in its entirety.

STATEMENT REGARDING FEDERALLY SPONSORED RESEARCH

This invention was made with government support under Grant Nos. MH036197, MH068318, MH074677, and DA017820, awarded by the National Institutes of Health. The government has certain rights in the invention.

FIELD OF THE DISCLOSURE

The present disclosure relates to medical imaging, and more specifically to exemplary apparatus, method, and computer readable-medium for imaging to detect and characterize neuropsychiatric and/or brain diseases and disorders.

BACKGROUND INFORMATION

Clinicians and researchers have long sought to use brain imaging measures as an aid in clinical diagnosis. For example, in prior attempts to use magnetic resonance imaging (MRI) in the diagnosis of neuropsychiatric illnesses, conventional anatomical measures of putative pathological involvement, such as the overall volume of a brain region or combination of brain regions, have not proven particularly useful, possibly because brain regions that can be identified on MRI scans can be anatomically and functionally heterogeneous. For any given brain region, therefore, opposing measures of pathological involvement in its various subregions, such as volume loss in one subregion and compensatory hypertrophy or normal volumes in another, when combined into an overall volume, can be dilute and highly variable, producing substantial overlap between diagnostic groups in the distributions of overall volumes. The overlap in distributions, in turn, can yield poor sensitivity and specificity when trying to use those measures for clinical diagnosis. (See, e.g., Peterson B S. *Form Determines Function: New Methods for Identifying the Neuroanatomical Loci of Circuit-Based Disturbances in Childhood Disorders*. Journal of the American Academy of Child and Adolescent Psychiatry. 2010; 49(6):533-5). However, recent methods in image processing can permit measures of local variation in the morphological features of brain subregions that can be more anatomically and functionally homogeneous than conventional overall volumes (see, e.g., Peterson B S. *Form Determines Function: New Methods for Identifying the Neuroanatomical Loci of Circuit-Based Disturbances in Childhood Disorders*. Journal of the American Academy of Child and Adolescent Psychiatry. 2010; 49(6):533-5), and can be associated with various neuropsychiatric disorders. (See, e.g., Peterson B S, Choi H A, Hao X, Amat J, Zhu H, Whiteman R, et al. *Morphology of the Amygdala and Hippocampus in Children and Adults with Tourette Syndrome*. Archives General Psychiatry. 2007; Peterson B S, Warner V, Bansal R, Zhu H, Hao X, Liu J, et al. *Cortical thinning in persons at increased familial risk for major depression*. Proc Natl Acad Sci USA. 2009; 106:6273-8; Toga A W, Thompson P A. *Mapping brain asymmetry*. Nature Neuroscience. 2003; 4(1):37-48; Luders E, Narr K, Thompson P, Woods R, Rex D, Jancke L, et al. *Mapping cortical gray matter in the young adult brain: Effects of gender*. NeuroImage. 2005; 26(2):493-501; Davatzikos C, Shen D, Gur R C, Wu X, Liu D, Fan Y, et al. *Whole-brain morphometric study of schizophrenia reveals a spatially complex set of focal abnormalities*. Arch General Psychiatry. 2005; 62:1218-27; and Csernansky J G, Schindler M K, Splinter N R, Wang L, Gado M, Selemon L D, et al. *Abnormalities of thalamic volume and shape in schizophrenia*. Am J Psychiatry. 2004; 161:896-902).

Machine-based learning and pattern classification can include constructing procedures that can automatically learn decision rules for classification from experimental datasets and then apply the learned rules to classify individuals in other datasets. (See, e.g., Duda R O, Hart P E. *Pattern Classification and Scene Analysis*: John Wiley & Sons; 1973). These methods generally belong to either supervised or unsupervised classes of learning. For example, the pairs of data points $\{(x_i, y_i), i=1, \ldots, n\}$, where $x_i \in R^m$ can be m-dimensional feature vectors and $y_i$ can be scalar-valued labels. The vectors $x_i$ can be brain measures and the labels $y_i$ can be clinical diagnoses. Supervised learning models can map between $x_i$ and $y_i$ using a parametric or nonparametric function $f(x)$, using a training sample to learn this function. The function can encode a decision rule or boundary that separates the feature vectors $x_i$ with the labels, $y_i$. If the labels $y_i$ are missing, then methods for unsupervised learning (e.g., also termed data mining or clustering procedures) can be used to discover natural groupings within the data. The validity of these groupings is preferably established using data outside of the dataset that has been mined to generate the groupings.

Extant methods for machine-based classification of individual brains in imaging datasets can generally be characterized as supervised. (See, e.g., Lao Z, Shen D, Xue Z, Karacali B, Resnick S, Davatzikos C. *Morphological classification of brains via high-dimensional shape transformations and machine learning methods*. NeuroImage. 2004; 21:46-57; Klöppel S, Stonnington C M, Chu C, Draganski B, Scahill R I, Rohrer J D, et al. *Automatic Classification of MR Scans in Alzheimer's Disease*. Brain. 2008; 131(3):681-9; Duchesnay E, Cachia A, Roche A, Rivière D, Cointepas Y, Papadopoulos-Orfanos D, et al. *Classification Based on Cortical Folding Patterns*. IEEE Trans on Medical Imaging. 2007; 26(4):553-65; Davatzikos C, Fan Y, Wu X, Shen D, Resnick S M. *Detection of prodromal Alzheimer's disease via pattern classification of MRI*. Neurobiol Aging. 2008; 29(4):514-23; Liu Y, Teverovskiy L, Carmichael O, Kikinis R, Shenton M, Carter C S, et al., editors. *Discriminative MR Image Feature Analysis for Automatic Schizophrenia and Alzheimer's Disease Classification* 2004: Springer-Verlag GmbH, Saint-Malo, France; Teipel S J, Born C, Ewers M, Bokde A L, Reiser M F, Moller H J. *Multivariate deformation-based analysis of brain atrophy to predict Alzheimer's disease in mild cognitive impairment*. NeuroImage. 2007; 38(1):13-24; Fan Y, Shen D, Davatzikos C. *Classification of structural images via high-dimensional image warping, robust feature extraction, and {SVM}*. Med Image Comput Comput Assist Interv Int Conf. 2005; 8:1-8; Kawasaki Y, Suzuki M, Kherif F, Takahashi T, Zhou S Y, Nakamura K,

*Multivariate voxel-based morphometry successfully differentiates schizophrenia patients from healthy controls.* NeuroImage. 2007; 34:235-42; Mourao-Miranda J, Bokde A L, Born C, Hampel H, Stetter M. *Classifying brain states and determining the discriminating activation patterns: Support Vector Machine on functional MRI data.* NeuroImage. 2005; 28:980-95; Herholz K, Salmon E, Perani D, Baron J C, Holthoff V, Frolich L. *Discrimination between Alzheimer dementia and controls by automated analysis of multicenter FDG PET.* NeuroImage. 2002; 17:302-16; Lerch J P, Pruessner J, Zijdenbos A P, Collins D L, Teipel S J, Hampel H, et al. *Automated cortical thickness measurements from MRI can accurately separate Alzheimer's patients from normal elderly controls.* Neurobiol Aging. 2006; 29(1):23-30; and Jack C R, Shiung M M, Gunter J L, O'Brien P C, Weigand S D, Knopman D S. *Comparison of different MRI brain atrophy rate measures with clinical disease progression in AD. Neurology.* 2004; 62:591-600).

These methods typically use quantitative imaging data and known clinical diagnoses to learn optimal decision boundaries in the feature space that best separate individuals with specific illnesses. The quantitative features that enter the training dataset (e.g., the Jacobian matrix of the deformation field) have generally been extracted from images using voxel based morphometry (VBM) (see, e.g., Ashburner J, Friston K J. *Voxel-based morphometry—the methods.* NeuroImage. 2000; 11(6):805-21; and Lochhead R A, Parsey R V, Oquendo M A, Mann J J. *Regional brain gray matter volume differences in patients with bipolar disorder as assessed by optimized voxel-based morphometry.* Biol Psychiatry. 2004; 55(12):1154-62), a technique that can provide automated, quantitative, and fine-grained morphological information about the brain. These imaging measures, however, can have limitations when trying to classifying individuals accurately into diagnostic categories. Such imaging measures typically assume that a voxel in a template space (e.g., a brain from a healthy individual) represents corresponding anatomical region in the brains across individuals. This assumption is typically unlikely to be true, even when the brains of differing individuals have been spatially normalized to the template using high-dimensional deformations. This can be because the smoothness constraints employed when warping a brain into template space, together with the variability in anatomy across individual brains, can limit the ability of the normalization procedures to match precisely the corresponding anatomical regions across individuals.

Together, these limitations can introduce imprecision when identifying the point-to-point correspondences across brains and can allow measures from any point in the brain that is warped to template space to be influenced by the variable features of brain regions at a distance remote from that point. Although more recently developed algorithms for high-order nonlinear warpings (see, e.g., Ou Y, Davatzikos C. *DRAMMS: deformable registration via attribute matching and mutual-saliency weighting.* Inf Process Med Imaging. 2009; 21:50-62) can reduce these inaccuracies, brain features near but outside the regions of interest can likely still influence the smoothed deformation fields. An alternate method that can provide more accurate identification of point correspondences across brain surfaces, independent of morphological features at points remote from those surfaces, can be to delineate the surface of each brain region precisely and independently from other brain regions, and then to normalize each region independently to the corresponding region of the template brain.

Classification procedures that have been generated using supervised, machine-based learning procedure can identify diagnostic groupings based on imaging data sampled simultaneously and independently at voxels scattered across the brain. This sampling can identify voxels that contribute importantly to accurate classification when generating the diagnostic algorithm, but they can rarely classify accurately when applied to imaging data that are independent of the data that generated the algorithm. (See, e.g., Haubold A, Peterson B S, Bansal R. *Progress in Using Brain Morphometry as a Diagnostic Tool for Psychiatric Disorders.* The Journal of Child Psychology and Psychiatry. In Press).

Accordingly, there may be a need to address at least some of the above-described deficiencies.

SUMMARY OF EXEMPLARY EMBODIMENTS

Exemplary embodiments of the present disclosure can provide diagnoses procedures using imaging-based measures, preferably alone, to improve the accuracy of the diagnosis, thereby reducing the costs associated with incorrect treatments. Exemplary methods, apparatus, and computer-readable medium can provide, for example, a semi-supervised learning procedure that can discover natural groupings of brains using, for example, the spatial patterns of variation in the morphology of the cerebral cortex and other brain regions. According to certain exemplary embodiments, split-half and leave-one-out cross-validation analyses can be used, for example, in large, human MRI datasets to assess the reproducibility and the diagnostic accuracy that those groupings provided. Exemplary embodiments of the present disclosure can facilitate, for example, discriminating the brains of persons who had one specific neuropsychiatric disorder from the brains of healthy participants and the brains of persons who have other neuropsychiatric disorders with high specificity and nearly perfect sensitivity. This can indicated that patterns of morphological variation across brain surfaces, extracted from MRI scans alone, for example, can successfully diagnose the presence of neuropsychiatric disorders. Extensions of these procedures are likely to provide biomarkers that can aid in identifying biological subtypes of those disorders, predicting disease course, and individualizing treatments for a wide range of neuropsychiatric illnesses.

Accordingly, according to certain exemplary embodiments of the present disclosure, it is possible to provide a fully automated procedure to diagnose individuals as having one of various neuropsychiatric illnesses using only anatomical MRI scans. This exemplary procedure can employ spherical wavelet analyses to encode the patterns of local variation in morphological features across multiple brain regions. It can also use machine-based hierarchical clustering techniques to discover natural groupings of the brains. These groupings can be highly reproducible and can be validated using computer-generated data and the classification procedures using large, real-world MRI datasets of persons with various neuropsychiatric disorders. These automated techniques can individualize and personalize clinical care for persons with neuropsychiatric illnesses by aiding in their clinical diagnoses, predicting disease course, and planning treatment.

Spherical wavelet analyses can be used to capture the patterns of spatial variation in these fine-grained, local morphological features across the brain, and machine-based learning can be used to identify natural groupings of brains that are based on those patterns of spatial variation. These groupings can map with high sensitivity and specificity to specific neuropsychiatric disorders. These techniques can be validated using both computer-generated datasets and large real-world datasets comprising many individuals across a variety of neuropsychiatric disorders.

Thus, according to certain exemplary embodiments of the present disclosure, exemplary method, system and computer-accessible medium can be provided for diagnosing at least one disease and/or a subtype within a disease. For example, it is possible to determine at least one region of interest, and obtain a plurality of data points associated with each of such region(s) of interest. It is also possible to identify a particular pattern of the data points across each of such region(s) of interest. Further, it is possible, e.g., using a computer arrangement, to determine a likelihood of the disease(s) and/or the subtype by comparing the particular pattern to at least one known pattern.

According to another exemplary embodiment of the present disclosure, the region(s) of interest can include a cortical mantle of a brain, a cortex of the brain, and/or a subcortical region of the brain. The data points can include a magnetic resonance imaging (MRI) image, a computed tomography (CT) image, an ultrasound image, a nuclear imaging image, an electroencephalogram (EEG) image, and/or a magnetoencephalogram (MEG) image. The pattern can be identified (i) based solely on the particular pattern the region(s) of interest, (ii) by implementing a mapping of the data points onto a sphere, and/or (iii) by applying a spherical wavelet transformation procedure.

In yet another exemplary embodiment of the present disclosure, spatial patterns of the particular pattern can be encoded as scaling coefficients, and wherein the likelihood can be determined using the scaling coefficients. The patterns can also be identified by obtaining naturalistic groupings within the data points. The data points can include raw image data, and/or represent information of at least one portion of a surface of a brain. The disease(s) can include autism, Tourette's syndrome, schizophrenia, bipolar disorder, attention deficit hyperactivity disorder, a major depressive disorder, stuttering, Parkinson's disease, premature birth, and/or toxic exposures.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying drawings showing illustrative embodiments of the present disclosure, in which.

Figure 1:
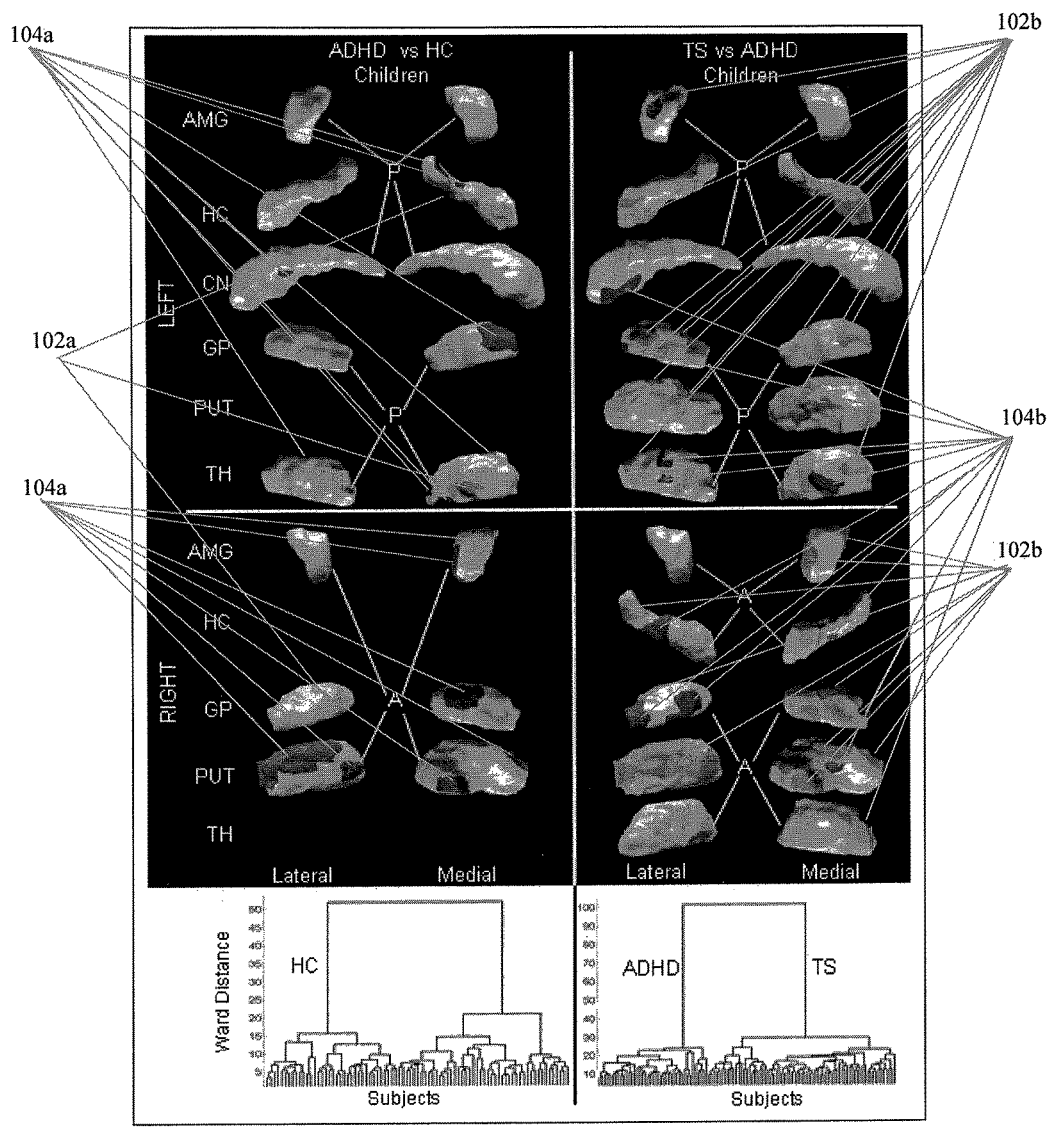
FIG. 1 is an illustration of exemplary classifications of a child as healthy or with ADHD and as having either TS or ADHD using certain exemplary embodiments of the present disclosure.

Throughout the drawings, the same reference numerals and characters, if any and unless otherwise stated, are used to denote like features, elements, components, or portions of the illustrated embodiments. Moreover, while the subject disclosure will now be described in detail with reference to the drawings, it is done so in connection with the illustrative embodiments. It is intended that changes and modifications can be made to the described exemplary embodiments without departing from the true scope and spirit of the subject disclosure.

DETAILED DESCRIPTION OF EXEMPLARY EMBODIMENTS

According to certain exemplary embodiments of the present disclosure, the hypothesis that identifying patterns of variation in morphological features that extend over many sets of contiguous voxels and across numerous brain regions can capture individual disturbances in the morphological features of neural circuits that are unique to each neuropsychiatric disorder and reduce the deleterious effects that noise at individual voxels has on the stability of the diagnostic procedure can be considered. Moreover, it is possible that identifying naturalistic groupings of brains according to their most robust and distinct patterns of circuit-based variation can be likely to yield more accurate and more stable diagnostic classifications based on those groupings, particularly when those procedures are, for example, applied to classifying brains in independent datasets.

Accordingly to exemplary embodiments of the present disclosure, procedures can be provided that can capture the patterns of spatial variation in these fine-grained, local morphological features across the surfaces of numerous brain regions in an attempt to represent neural circuit-based patterns of variation in local morphology. The exemplary patterns of spatial variations can be analyzed using machine-based learning techniques to identify natural groupings of brains. These naturalistic groupings can map with high sensitivity and specificity to specific neuropsychiatric disorders. Computer-generated datasets (e.g., by a hardware computer arrangement) can be used to validate this general approach, and human MRI datasets including many individuals across a variety of neuropsychiatric disorders can further be used to validate and reproduce the specific diagnostic algorithms that classify brains with high sensitivity and specificity as belonging to persons of one specific diagnostic group rather than another.

According to certain exemplary embodiments of the present disclosure, a procedure can be provided to identify valid, naturalistic groupings of the brains based on the spatial patterns of local variation in the morphological features across the surfaces of numerous cortical and subcortical brain regions, with the aim of identifying neural circuit-based disturbances that are unique to specific neuropsychiatric disorders. For example, the boundary of each brain region can be manually delineated by an expert neuroanatomist using validated and reliable procedures published elsewhere, which can provide surface delineations that are preferably independent of the influences of other regions. (See, e.g., Peterson B S, Choi H A, Hao X, Amat J, Zhu H, Whiteman R, et al. *Morphology of the Amygdala and Hippocampus in Children and Adults with Tourette Syndrome*. Archives General Psychiatry. 2007; Peterson B S, Warner V, Bansal R, Zhu H, Hao X, Liu J, et al. *Cortical thinning in persons at increased familial risk for major depression*. Proc Natl Acad Sci USA. 2009; 106:6273-8; Plessen K J, Bansal R, Zhu H, Whiteman R, Quackenbush G A, Hugdahl K, et al. *Hippocampus and amygdala morphology in Attention-Deficit/Hyperactivity Disorder*. Arch Gen Psychiatry. 2006; 63:795-807; Peterson B S, Thomas P, Kane M J, others a. *Basal ganglia volumes in patients with Gilles de la Tourette syndrome*. Arch Gen Psychiatry. 2003; 60:415-24; and Peterson B S, Riddle M A, Cohen D J, Katz L D, Smith J C, Hardin M T, et al. *Reduced basal ganglia volumes in tourette's syndrome using three-dimensional reconstruction techniques from magnetic resonance images*. Neurology. 1993; 43(5):941-9). The delineated brain regions can be then warped independently into template space unique to each region, free of the influences of the morphological features of other brain regions. A conformal mapping can then be used to transfer these local morphological variations from the surface of the template region onto a unit sphere, where a spherical wavelet transform can be applied to characterize the spatial pattern of this local variation and to reduce the dimensionality of the dataset. (See, e.g., FIG. 5). Scaling coefficients can encode the spatial pattern of variation at progressively lower spatial resolutions so as to capture both local and more global features of morphological variation. (See, e.g., FIG. 5). The exemplary procedure(s) can be validated using computer-generated and real-world human datasets of patients with various neuropsychiatric disorders, including, for example, individuals either with Tourette's Syndrome (TS), Attention-Deficit/Hyperactivity Disorder (ADHD), Bipolar Disorder (BD), or Schizophrenia (SZ), and persons at high or low familial risk for Major Depressive Disorder (MDD), as well as a large sample of healthy children (HC) and healthy adult (HA) control participants.

For example, according to exemplary embodiments of the present disclosure, exemplary classification method, apparatus, system, and computer-accessible medium can be provided, which can be used to implicate specific neural circuits in various neuropsychiatric illnesses. Neuropsychiatric illnesses can include brain disorders that can be conceptualized as disturbances of neural circuits in the brain. (See, e.g., Peterson B S. Form Determines Function: *New Methods for Identifying the Neuroanatomical Loci of Circuit-Based Disturbances in Childhood Disorders*. Journal of the American Academy of Child and Adolescent Psychiatry. 2010; 49(6):533-5; and Insel T, Cuthbert B, Garvey M, Heinssen R, Pine D S, Quinn K, et al. Research Domain Criteria (RDoC): *Toward a New Classification Framework for Research on Mental Disorders*. Am J Psychiatry. 2010; 167(7)). These disturbances therefore can be manifested as abnormalities in subnuclei that are distributed in and across numerous brain regions. The exemplary classification procedure can identify these subnuclei and can encode the spatial pattern of their disturbances to accurately classify an individual among neuropsychiatric illnesses. For a specific disorder, the exemplary method and/or procedure can identify the spatial pattern that can accurately classify individuals with the largest sensitivity and specificity, thereby associating that spatial pattern of abnormalities with the disorder or a subtype within a disorder. These abnormal subnuclei can include one or more neural circuits, facilitating implication of those neural circuits in the neuropsychiatric disorders.

The exemplary procedures according to the present disclosure can use a training dataset prior to their validation in an independent dataset. In the training dataset, scaling coefficients that differed (e.g., $p<10^{-7}$, see, e.g., FIG. 8) between two diagnostic groups of interest can be selected as feature vectors. A hierarchical clustering techniques can be applied to those selected scaling coefficients in order to identify two natural groupings of the brains that were based on the similarity of their morphological features. Those exemplary features can be presumed to support similar computational and behavioral functions, and that the brains that shared them can map more accurately to biologically based groupings of illnesses than would the morphological features identified by prior classification schemes that were based only on clinical symptoms. A clinical diagnostic label can be assigned by a simple majority rule to each of the two groups of brains identified by the training procedure, so that the known clinical diagnosis that affected the majority of participants in each group can be provided its diagnostic label.

These naturalistic groupings can be validated by assessing the accuracy of the procedure to classify brains drawn from an independent dataset of persons who had known clinical disorders. A diagnosis can be assigned to brains in the validation dataset by assessing which of the two diagnostic groups in the training dataset had morphological features most similar to its own, and then transferring the diagnostic label from that group to that individual brain. This similarity can be assessed by determining Ward's distance from the feature vector of the brain being classified to the average feature vector of brains in each of the two groups identified in the training dataset.

According to certain exemplary embodiments of the present disclosure, the naturalistic groupings can be validated, for example, using both leave-one-out (LOO) cross-validation analyses and 10 independent split-half replication analyses. In addition, the exemplary misclassification rates can be determined using LOO cross-validation applied to the random halves of data generated in the split-half analyses. In each of the 10 split-half analyses, for example, (a) the imaging datasets can be partitioned randomly into two halves, the training set and the test set, (b) the classification procedure can be generated using the training set, and (c) the performance of the classification procedure can be evaluated, for example, using the second, independent test half of the dataset. Automated, computer-based procedures can assign a brain in the second test dataset to one of the two putative diagnostic groups identified in the training dataset, for example, by assessing which of the two groups had morphological features most similar to its own. The brain can be considered to be misclassified if its diagnosis differed from that of the group label assigned in the training dataset. Assigning each brain in the test dataset one at a time to a putative diagnostic label can facilitate computing misclassification rates in a dataset that was entirely independent of the training dataset that generated the classification procedure. These split-half procedures can be repeated independently for every pair of the 10 training and test datasets, thereby generating 10 independent estimates of the misclassification rates for each pair of clinical diagnoses can be discriminated (e.g. TS vs HC). The mean and standard deviations of the misclassification rates can be determined across these multiple split-half and LOO cross-validations, which can then be used to calculate the sensitivity and specificity of the diagnostic procedure. It can be important that even though the features entering the classification procedures and the labels assigned to the subsequent naturalistic groupings of brains can be determined using previously known clinical diagnoses, it can be the hierarchical clustering procedure alone, operating without information about clinical diagnoses and preferably based solely on the morphological features shared across brains within each dataset, that can generate the naturalistic groupings of brains used in the following validation of MRI-based diagnoses.

Figure 6:
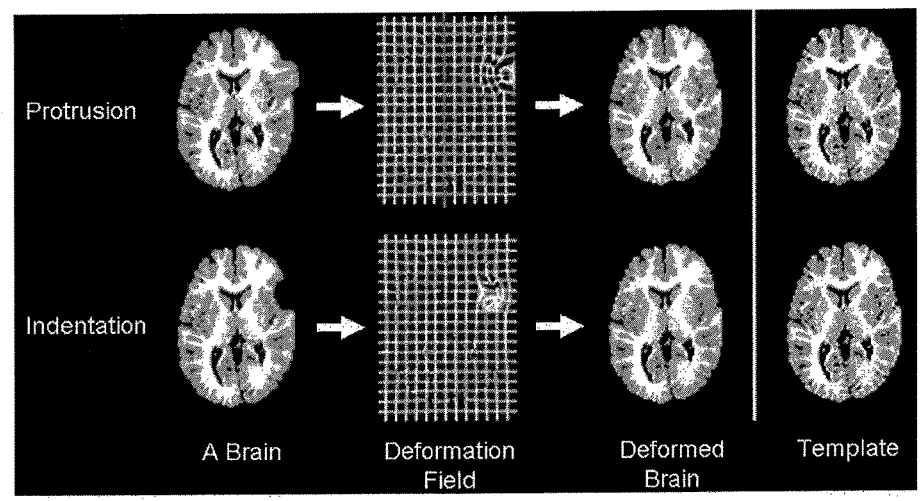
FIG. 6 are a set of images of warping a deformed brain to a template brain according to certain exemplary embodiments of the present disclosure.
Figure 7:
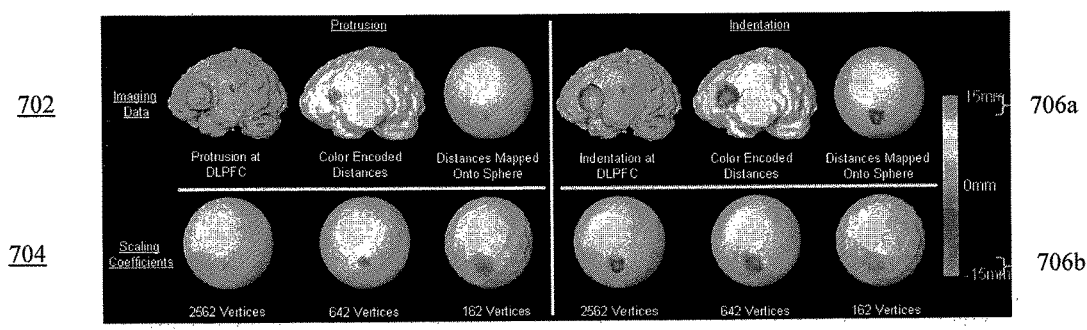
FIG. 7 is an illustration of exemplary the deformations at a dorsolateral prefrontal cortex (DLPFC) in the exemplary template brain according to certain exemplary embodiments of the present disclosure.

According to certain exemplary embodiments of the present disclosure, computer-generated datasets can be used to test the ability of the exemplary classification scheme to identify natural groupings of brains that contained differing morphological features, deformations of known-size placed at pre-specified locations on the surfaces of brains from healthy participants (see, e.g., FIGS. 6 and 7). The exemplary classification procedures can discriminate and identify the brains with and without the known deformation (see, e.g., FIGS. 9 and 10).

The performance of the exemplary classification schemes can be assessed in patients with known gold-standard clinical diagnoses, for example, using both leave-one-out cross-validation analyses and ten independent split-half replication analyses that partitioned the imaging datasets randomly into two halves. The datasets that can be used to generate and validate the classification procedures can include, for example, 40 healthy adults (HA), 42 healthy children (HC), 41 children with Attention Deficit Hyperactivity Disorder (ADHD), 65 adults with Schizophrenia (SZ), 36 adults and 71 children with Tourette Syndrome (TS), and 26 adults with Bipolar Disorder (BD) I. Whether the scheme could generate a classification procedure that would distinguish between 131 individuals who were at either a high (HR) or a low (LR) familial risk for major depressive disorder (MDD) can also be assessed. (See, e.g., Peterson B S, Warner V, Bansal R, Zhu H, Hao X, Liu J, et al. *Cortical thinning in persons at increased familial risk for major depression*. Proc Natl Acad Sci USA. 2009; 106:6273-8). In the exemplary split-half replication analyses using the human datasets, training can include, for example 13 BD and 20 HC adults, 32 SZ and 20 HC adults, 18 TS and 20 HC adults, 20 ADHD and 21 HC children, 35 TS and 21 HC children, and 32 LR and 33 HR individuals selected randomly from the exemplary cohorts, and the test set can include the other half of the participants in each of these cohorts.

If a dataset can indeed be clustered into natural groupings, then the distances between groups is typically much larger than the distances between participants within groups. These distances can be compared formally in the exemplary hierarchical clustering procedure by computing, for example, the Cophenetic Correlation Coefficient (CPCC), the coefficient for the correlation of the distance between any two feature vectors ($x_1$, $x_2$) with the distance between the two clusters ($C_1$, $C_2$) that can be merged when those two feature vectors were first placed in the same cluster. The possible values of the CPCC range from −1 to 1, with larger positive values indicating a good match between the data values and the hierarchy generated in the clustering procedure. CPCC's for the datasets can be consistently very high (e.g., near 0.7) for the clustering of data generated using Ward's linkage. However, the CPCC can typically be sensitive to the linkage method used to form the hierarchy, and is therefore not necessarily an ideal metric. (See, e.g., Holgersson M. *The limited value of cophenetic correlation as a clustering criterion Pattern Recognition*. 1979; 10(4):287-95; and Rohlf F J. *Adaptive hierarchical clustering schemes*. Systematic Zool. 1970; 19:58-82).

The exemplary classification procedures according to certain exemplary embodiments of the present disclosure can discriminate, for example, the brains of persons with a specific neuropsychiatric disorder from the brains of healthy persons, and from the brains of persons who had differing neuropsychiatric disorders, with high sensitivities and specificities (see, e.g., Table 1). They can discriminate, for example, the brains of children with ADHD from HC with 93.6% sensitivity and 88.5% specificity (see, e.g., FIG. 1, left); children with TS from children with ADHD with 99.83% sensitivity and 99.5% specificity (see, e.g., FIG. 1, right); adults with BD from HA with 100% sensitivity and 96.4% specificity (see, e.g., FIG. 2, 1st column); adults with SZ from adults with TS with 99.99% sensitivity and 100% specificity (see, e.g., FIG. 2, 2nd column); adults with SZ from adults with BD with 99.99% sensitivity and 100% specificity (see, e.g., FIG. 2, 3rd column); adults with SZ from healthy adults with 93.1% sensitivity and 94.5% specificity (see, e.g., FIG. 2, 4th column); adults with TS from HA with 83.2% sensitivity and 90% specificity (see, e.g., FIG. 3, left); children with TS from HC with 94.6% sensitivity and 79% specificity (see, e.g., FIG. 3, right); and participants at HR for depression from those at LR for depression with 81% sensitivity and 71% specificity (see, e.g., FIG. 4). The positive predictive values for each of these classifications can be high, e.g., ranging from 0.89 to 1.0, except for a value of 0.74, for example, when classifying persons at HR or LR for depression, which may not be surprising, given that the exemplary classifications were of people at risk for developing an illness and not those with an already-established disorder.

Specificities can tend to be somewhat lower than sensitivities when classifying patient groups against healthy participants, indicating that misclassifications can tend to be more frequent in the healthy participants. Misclassification of healthy individual can derive from their carrying a brain feature that could place them at greater risk for developing an illness, even though that illness has never become manifest. Brain-based vulnerability in the exemplary sample of participants at high or low familial risk for depression has been shown. (See, e.g., Peterson B S, Warner V, Bansal R, Zhu H, Hao X, Liu J, et al. *Cortical thinning in persons at increased familial risk for major depression*. Proc Natl Acad Sci USA. 2009; 106:6273-8). In addition, the performance of three-way classifications can be poor, likely because of the limited sample sizes. Therefore, according to certain exemplary embodiments of the present disclosure, an iterative, two-step classification strategy which can first discriminate patients from healthy controls, and then the two patient groups from one another, can achieve a highly accurate three-way classification, can be provided. The adjusted exemplary misclassification rates for the three-way classifications can be, for example: 0 for healthy adult, 0.14 for BD adult, and 0.14 for SZ adult; and 0.10 for healthy adult, 0.168 for TS adult, and 0.0245 for SZ adult. (See, e.g., FIGS. 1-4 and 11; and Table 1).

According to certain exemplary embodiments of the present disclosure, a method can be provided that can use anatomical brain images alone to diagnose neuropsychiatric disorders automatically and with excellent sensitivity and specificity. This exemplary method can discover natural groupings of people who share similar spatial patterns of local variation in the morphological features of both cortical and subcortical brain regions. The shared local variations in surface morphological features can differ significantly across participants who had differing neuropsychiatric disorders. The groupings can be generate using these brain measures to classify an individual as having one of among numerous disorders with high accuracy.

Although other studies have applied various machine-based classification techniques to brain imaging measures in attempts to diagnose people with various neuropsychiatric illnesses, none have achieved a similar degree of accuracy across as wide a range of neuropsychiatric illnesses as those exemplary procedures according to exemplary embodiments of the present disclosure. These exemplary successful results can be attributed to several unique features of the exemplary classification strategy. For example, according to certain exemplary embodiments of the present disclosure, these exemplary classification techniques can be applied across multiple individually and accurately defined brain regions, rather than to a single image of the entire brain, as is common using techniques such as voxel-based morphometry. Additionally, conformal mapping and spherical wavelet transforms of the exemplary imaging measures can be used to capture spatial patterns of variation in local morphological features, rather than relying on individual and group variability of those local features alone when measured at single isolated voxels. Further, hierarchical clustering techniques can be applied to the scaling coefficients of the wavelet transforms in order to identify natural groupings of spatial patterns of variation in morphological features of the brain across participants, rather than applying those clustering techniques to measures at each individual voxel of the brain. This approach can classify brains according to normal and pathological spatial variations in morphological features and can thereby identify distributed, circuit-based disturbances across the brain associated with specific neuropsychiatric illnesses. (See, e.g., Peterson B S. *Form Determines Function: New Methods for Identifying the Neuroanatomical Loci of Circuit-Based Disturbances in Childhood Disorders*. Journal of the American Academy of Child and Adolescent Psychiatry. 2010; 49(6):533-5; and Insel T, Cuthbert B, Garvey M, Heinssen R, Pine D S, Quinn K, et al. *Research Domain Criteria (RDoC): Toward a New Classification Framework for Research on Mental Disorders*. Am J Psychiatry. 2010; 167(7)). The high diagnostic sensitivity and specificity of the exemplary classification procedures across a wide range of disorders and across cohorts of varying sizes, demographic characteristics, and treatment histories, and even in a high risk sample, most of whom were typically unaffected by and untreated for manifest illness, can demonstrate the exceptional robustness of this method for classifying an individual as having one among various neuropsychiatric disorders.

In addition, previous machine-based classification procedures typically partitioned the feature space into regions that map to various diagnoses by learning complex boundaries that typically require estimation of a large number of parameters in relatively small groups of participants who have one among several possible diagnoses. These methods also have generally used the labeled data (e.g., pairs of feature vector and its corresponding label) to learn the boundaries that minimize misclassification in the labeled data. The determination of the complexity is typically a trade-off between correctly classifying participants using training data and correctly labeling a new individual. The optimum amount of trade-off is typically difficult to be determined quantitatively, and therefore ad hoc qualitative procedures are typically applied to determine the complexity of these boundaries. In contrast, the exemplary method according to certain exemplary embodiments of the present disclosure can discover the natural structure within the data and therefore can more accurately classify an individual among disorders for at least the following two reasons. First, the exemplary method can automatically (e.g., using a hardware computer processing arrangement) generate natural groupings of data without using the clinical diagnoses of the participants. Further, participants with differing diagnoses near the boundary can naturally form groups and therefore the combination of these participants into a single group can yield groupings that are clinically more meaningful. Thus, the exemplary method can automatically discover the structure in the imaging dataset such that participants in each group have similar local variations in brain measures and have similar clinical measures, thereby classifying more accurately an individual among various neuropsychiatric disorders.

Potential sources of error in classification can include errors in the methods for extracting feature vectors from the images. Errors in extracted features can increase the variance and therefore can reduce the statistical power of the exemplary method for accurately classifying and diagnosing individual brains. However, it has been shown that the exemplary methods for spatial normalization of brain regions to the template brain can be highly accurate. (See, e.g., Bansal R, Staib L H, Wang Y, Peterson B S. ROC-based assessments of 3D cortical surface-matching algorithms. Neuroimage. 2005; 24:150-62). Similarly, the methods that can be used to map surface features conformally onto a unit sphere have also been previously validated. (See, e.g., Angenent S, Haker S, Tannenbaum A, Kikinis R. On the Laplace-Beltrami operator and brain surface flattening. IEEE Transactions on Medical Imaging. 1999; 18(8):700-11). Finally, the scaling coefficients can be computed using the well-validated wavelet transform. Thus, the exemplary methods can be applied in each of the various steps used for feature extraction can be preferably robust, and they can compute highly accurate scaling coefficients 9 e.g., using the hardware computer processing arrangement). Another source of potential error in classification can be the overlap of the feature spaces across disorders. The structures discovered in the exemplary datasets can be validated by comparing visually and quantitatively the distances between groups and between participants within groups using dendrograms. Those distances can indicate that the exemplary groupings can be quite clear and distinct. The groupings can also be validated using leave-one-out and split-half cross validation procedures, which generally demonstrated very low rates of misclassification in independent datasets and a high level of reproducibility in generating the procedures that can be used for group classifications.

The exemplary ability to use morphological features of the brain to classify and diagnose individuals accurately as having a specific neuropsychiatric illness can suggest that the brains of the individuals who share a primary clinical diagnosis also likely share a common core neurobiological substrate for that illness, despite the widely known and undeniable etiologic heterogeneity of virtually all neuropsychiatric disorders. This shared substrate does not mean that the brains of people who have a given neuropsychiatric diagnosis are identical. Indeed, a visual inspection of the classification trees shows evidence for variability of feature vectors within diagnostic groupings, and even evidence for the presence of morphological subtypes within clusters of a single clinical diagnosis. Such variability can represent either the presence of differing etiologic subtypes within a single diagnostic label or the presence of additional, co-occurring illnesses for persons who share a single primary clinical diagnosis, which is common in clinical samples.

According to further exemplary embodiments of the present disclosure, a semi-supervised method for machine learning can be provided to identify natural groupings of people in the spatial variation of fine-grained, local morphological features across their brains. Machine-based learning and pattern classification can, for example, seek to construct procedures that automatically learn decision rules for classification from experimental datasets, and then it can apply the learned rules to classify individuals in other datasets. (See, e.g., Duda R O, Hart P E. Pattern Classification and Scene Analysis: John Wiley & Sons; 1973). These exemplary methods generally belong to either supervised or unsupervised classes of learning. For example, the pairs of data points $\{(x_i,y_i), i=1, \ldots, n\}$, where $x_i \in R^m$ can be m-dimensional feature vectors and $y_i$ can be scalar-valued labels. The vectors $x_i$ can be brain measures and the labels $y_i$ can be clinical diagnoses. Supervised learning can use a training sample to learn the mapping between $x_i$ and $y_i$ using a parametric or nonparametric function, $f(x)$. This function can, for example, encode a decision rule, or boundary, that preferably optimally separates the feature vectors $x_i$ using the labels, $y_i$. If the labels $y_i$ are missing, then methods for unsupervised learning (also termed data mining or clustering procedures) can be used to discover natural groupings within the data. Such exemplary method can be considered semi-supervised because leave-one-out cross validation can be applied, for example, to select a set of features that differs significantly between groups of individuals who are already clinically diagnosed, and then hierarchical clustering can be applied, for example, to the feature vectors to discover naturalistic groupings of individuals in the dataset. The validity of these naturalistic groupings can be assessed by applying leave-one-out and split-half cross-validation procedures to datasets that can be independent of those that have been mined to generate the groupings.

Exemplary Participants

Exemplary experiments implementing/using certain exemplary embodiments of the present disclosure are discussed below. Exemplary participants in an exemplary experiment implementing/using certain exemplary embodiments of the present disclosure provided written informed consent. For example, all were free of a history of neurological illness, substance dependence, sustained loss of consciousness, and significant medical illness. Diagnostic interviews can include the Schedule for Affective Disorders and Schizophrenia for School-Age Children: Present and Lifetime Version. (See, e.g., Kaufman J, Birmaher B, Brent D, Rao U, Flynn C, Moreci P, et al. *The Schedule for Affective Disorders and Schizophrenia for School-Age Children: Present and Lifetime Version (K-SADS-PL): initial reliability and validity data*. J Am Acad Child Adolesc Psychiatry. 1997; 36:980-8). Diagnostic interviews in adults can be performed using either the Schedule for Affective Disorders and Schizophrenia (see, e.g., Endicott J, Spitzer R L. *A diagnostic interview: the Schedule for Affective Disorders and Schizophrenia*. Arch Gen Psychiatry. 1978; 35:837-44) or the Structures Clinical Interview for DSM-IV Axis I Disorders (SCID) (Version 2.0). (See, e.g., First M B, Spitzer R L, Gibbon M, Williams J B W. *Structured Clinical Interview for DSM-IV Axis I & II Disorders (Version 2.0)*. New York: New York State Psychiatric Institute. 1995). Consensus diagnosis based on a best-estimate procedure that involved an independent review of the clinical and structured interviews by two experienced clinicians can be used to establish the final diagnosis for all participants. (See. e.g., Blumberg H P, Leung H-C, Wexler B, Skudlarski P, Lacadie C M, Anand A, et al. *An fMRI study of bipolar disorder. State-and trait-related dysfunction in ventral prefrontal cortices*. Arch Gen Psychiatry. 2003; 60:601-9; Blumberg H P, Kaufman J, Martin A, Whiteman R, Gore J C, Charney D S, et al. *Amygdala and hippocampus volumes in adolescents and adults with Bipolar Disorder*. Arch Gen Psychiatry. 2003; 60:1201-8; Leckman J F, Sholomskas D, Thompson D, Belanger A, Weissman M. *Best estimate of lifetime psychiatric diagnosis: a methodological study*. Arch Gen Psychiatry. 1982; 39:879-83; and Peterson B S, Warner V, Bansal R, Zhu H, Hao X, Liu J, et al. *Cortical thinning in persons at increased familial risk for major depression*. Proc Natl Acad Sci USA. 2009; 106:6273-8).

Exemplary Healthy Participants

Imaging data can be acquired, for example, in 42 healthy children (e.g., 18 males, age 10.5±2.43 years) and 40 healthy adults (22 males, age 32.42±10.7 years). Additional exclusion criteria for healthy participants can include a lifetime or a current DSM-IV Axis 1 or 2 disorder, and IQ<80 as measured by the WISC-III (see, e.g., Wechsler D. *WISC-III Manual*. Canadian Supplement. Toronto: Psychological Corporation 1996), WAIS (see, e.g., Wechsler D. *Wechsler Adult Intelligence Scale-III*. New York: Psychological Corporation 1991), or Kaufmann-Brief Intelligence Test (see, e.g., Grados J J, Russo-Garcia K A. *Comparison of the Kaufman Brief Intelligence Test and the Wechsler Intelligence Scale for Children-Third Edition in economically disadvantaged African American youth*. J Clin Psychol. 1999; 55(9):1063-71).

Exemplary Tourette Syndrome (TS) Participants

Imaging data can be acquired, for example, in 71 TS children (e.g., 59 males, age 11.19±2.2 years) and 35 TS adults (21 males, age 37.34±10.9 years). The participants can be ascertained through the local chapter of the Tourette Syndrome (TS) Association, and through the Tic Disorder Clinic of the Yale Child Study Center, New Haven, Conn. Diagnoses can be supplemented using the Schedule for Tourette and Other Behavioral Syndromes (see, e.g., Pauls D L, Hurst C R. *Schedule for Tourette and Other Behavioral Syndromes*. New Haven, Conn. 1996), and ratings of current and worst ever severity of tic, OCD, and ADHD symptoms using the Yale Global Tic Severity Scale (see, e.g., Leckman J F, Riddle M A, Hardin M T, Ort S I, Swartz K L, Stevenson J, et al. *The Yale Global Tic Severity Scale: initial testing of a clinician-rated scale of tic severity.* J Am Acad Child Adolesc Psychiatry. 1989; 28:566-73), the Yale-Brown Obsessive Compulsive Scale (see, e.g., Goodman W K, Price L H, Rasmussen S A, Mazure C, Fleischmann R L, Hill C L, et al. *The Yale-Brown Obsessive Compulsive Scale, I: development, use, and reliability.* Arch Gen Psychiatry. 198; 46:1006-11; Goodman W K, Price L H, Rasmussen S A, Mazure C, Delgado P, Heninger G R, et al. *Yale-Brown Obsessive Compulsive Scale, II: validity.* Arch Gen Psychiatry. 1989; 46:1012-8; and Scahill L, Riddle M A, McSwiggin-Hardin M, Ort S I, King R A, Goodman W K, et al. *Children's Yale-Brown Obsessive Compulsive Scale: reliability and validity.* J Am Acad Child Adolesc Psychiatry. 1997; 36:844-52), and the DuPaul-Barkley Attention-Deficit/Hyperactivity Disorder (ADHD) rating scale (see, e.g., DuPaul G J. *Parent and teacher ratings of ADHD symptoms: psychometric properties in a community-based sample.* J Clin Child Psychol. 1991; 20:245-53).

Exemplary ADHD Participants

In the exemplary cohort 41 ADHD children can be imaged (e.g., 33 males, age 12.6±3.18 years). The participants can be recruited, for example, through the general outpatient clinic at the Yale Child Study Center or through advertisements with a local chapter of ChADD (Children with Attention Deficit Disorder). Diagnostic assessments can be supplemented, for example, using the Conners ADHD Parent and Teacher Rating Scales (see, e.g., Conners C K, Sitarenios G, Parker J D, Epstein J N. *The revised Conners' Parent Rating Scale (CPRS-R): factor structure, reliability, and criterion validity.* J Abnorm Child Psychol. 1998; 26:257-68; and Conners C K, Sitarenios G, Parker J D, Epstein J N. *Revision and restandardization of the Conners Teacher Rating Scale (CTRS-R): factor structure, reliability, and criterion validity.* J Abnorm Child Psychol. 1998; 26:279-91) and the DuPaul-Barkley ADHD rating scale (see, e.g., DuPaul G J. *Parent and teacher ratings of ADHD symptoms: psychometric properties in a community-based sample.* J Clin Child Psychol. 1991; 20:245-53). ADHD subjects with lifetime of Obsessive Compulsive Disorder (OCD), Tourette Syndrome or Tic disorder, and premature birth (gestation≤36 weeks) can be excluded from this group.

Exemplary Bipolar Disorder (BD) I Participants

The cohort can include 26 adults with BD (e.g., 11 males, age 37.65±10.35 years), who can be identified from general psychiatry outpatient clinics. The participants can be recruited either at the Yale School of Medical Center or the Veterans Affairs Connecticut Healthcare System, or referred by the practitioner. (See, e.g., Blumberg H P, Krystal J H, Bansal R, Martin A, Dziura J, Durkin K, et al. *Age, Rapid-Cycling, and Pharmacotherapy Effects on Ventral Prefrontal Cortex in Bipolar Disorder: A Cross-Sectional Study* Biol Psychiatry. 2006; 59(7):611-8). During the history of their illness, the participants can have met DSM-IV criteria for having had a manic episode lasting at least one week.

Exemplary Schizophrenia (SZ) Participants

Imaging data can be acquired in 65 adults with SZ (e.g., 41 males, age 42.16±8.71 years). The participants can be identified from general psychiatry outpatient clinics who met DSM-IV criteria for schizophrenia. The participants may have been on their medication for at least 30 days and had not abused substances for at least 60 days. Diagnostic assessments can be supplemented using the Positive and Negative Symptom Scale for Schizophrenia. (See, e.g., Wexler B E, Zhu H, Bell M D, Nicholls S, S, Fulbright R K, Gore J C, et al. *Neuropsychological Near Normality and Brain Structure Abnormality in Schizophrenia.* Am J Psychiatry. 2009; 166:189-95; and Kay S R, Fiszbein A, Opler L. *The Positive and Negative Symptom Scale for Schizophrenia.* Schizophr Bull. 1987; 13:261-76).

Exemplary Participants at High or Low Risk for Major Depressive Disorder (MDD)

These individuals can belong to a 3-generation cohort in which the first two generations could have been followed for more than 22 years. In the first generation ("G1"), one group of adults can be clinically ascertained during treatment of moderate to severe, recurrent, and functionally debilitating MDD; the other group can be a sample of matched control adults from the same community who had no discernible lifetime history of depression. The biological offspring of the first generation comprised the second generation ("G2"), and the offspring of the second generation can make up the third generation ("G3"). (See, e.g., Peterson B S, Warner V, Bansal R, Zhu H, Hao X, Liu J, et al. *Cortical thinning in persons at increased familial risk for major depression.* Proc Natl Acad Sci USA. 2009; 106:6273-8; and Weissman M M, Wickramaratne P, Nomura Y, Warner V, Verdeli H, Pilowsky D J, et al. *Families at High and Low Risk for Depression.* Arch Gen Psychiatry. 2005; 62:29-36). The participants identified at "high risk" for developing MDD can be those members of G2 and G3 who were biological descendants of the MDD group in G1 and those identified at "low risk" can be the G2 and G3 biological descendants of the unaffected control group in G1. Imaging data can be acquired, for example, for 131 individuals in G3: 66 (e.g., 12 children, 54 adults) in the high risk group, and 65 in the low risk group (e.g., 31 children, 34 adults).

Exemplary MRI Pulse Sequence

T1-weighted MR images can be acquired, for example, on a 1.5 Tesla GE scanner using a sagittal spoiled gradient recall sequence (e.g., TR=24 msec, TE=5msec, 45° flip, frequency encoding S/I, no wrap, 256×192 matrix, FOV=30 cm, 2 excitations, slice thickness=1.2 mm, 124 contiguous slices). This sequence can be selected to provide superior signal-to-noise and contrast-to-noise ratios in high-resolution images having nearly isotropic voxels (1.171×1.171× 1.2 mm).

Exemplary Isolation of the Brain and Defining ROIs

The brain can be isolated from non-brain tissue and various brain regions can be defined using valid and highly reliable methods. (See, e.g., Peterson B S, Riddle M A, Cohen D J, Katz L D, Smith J C, Hardin M T, et al. *Reduced basal ganglia volumes in tourette's syndrome using three-dimensional reconstruction techniques from magnetic resonance images.* Neurology. 1993; 43(5):941-9; Kates W R, Abrams M T, Kaufman W E, Breiter S N, Reiss A L. *Reliability and validity of MRI measurement of the amygdala and hippocampus in children with fragile X syndrome.* Psychiatry Res: Neuroimaging. 1997; 75:31-48; and Watson C, Andermann F, Gloor P, Jones-Gotman M, Peters T, Evans A, et al. *Anatomic basis of amygdaloid and hippocampal volume measurement by magnetic resonance imaging.* Neurology. 1992; 42(9):1743-50). For example, images can be flipped randomly, for example, in the left-right direction prior to region definition and the flips can be reversed following region definition to ensure the absence of operator bias in defining structures in each hemisphere. Inhomogeneities can be removed in image intensity (see, e.g., Sled G J, Zijdenbos A P, Evans A C. *A Nonparametric Method for Automatic Correction of Intensity Nonuniformity in MRI Data.* IEEE Trans of Medical Imaging. 1998; 17(1): 87-97) and the brain can be isolated from non-brain tissue using an automated tool for brain extraction (see, e.g., Shattuck D W, Leahy R M. BrainSuite: An Automated Cortical Surface Identification Tool. Medical Image Analysis. 2002; 8(2):129-42) together with manual editing. Various orthogonal views can be used to remove connecting dura in each slice of the image. Cortical gray matter can be defined, for example, using a combination of automated thresholding of gray and white matter and manual editing in orthogonal views. Subcortical nuclei can be defined using manual tracings. Intraclass correlation coefficient (ICC) on 10 images across 2 raters to measure the interrater reliabilities for the morphometric measurements can be greater than, for example (1) 0.91 for the hippocampus (see, e.g., Peterson B S, Choi H A, Hao X, Amat J, Zhu H, Whiteman R, et al. *Morphology of the Amygdala and Hippocampus in Children and Adults with Tourette Syndrome*. Archives General Psychiatry. 2007), (2) 0.89 for the amygdala (see, e.g., Peterson B S, Choi H A, Hao X, Amat J, Zhu H, Whiteman R, et al. *Morphology of the Amygdala and Hippocampus in Children and Adults with Tourette Syndrome*. Archives General Psychiatry. 2007), (3) 0.95 for the caudate and putamen nuclei (see, e.g., Peterson B S, Thomas P, Kane M J, others a. Basal ganglia volumes in patients with Gilles de la Tourette syndrome. Arch Gen Psychiatry. 2003; 60:415-24); (4) 0.90 for the globus pallidus (see, e.g., Peterson B S, Thomas P, Kane M J, others a. *Basal ganglia volumes in patients with Gilles de la Tourette syndrome. Arch Gen Psychiatry*. 2003; 60:415-24). (5) 0.99 for the cerebral hemispheres (see, e.g., Peterson B S, Thomas P, Kane M J, others a. *Basal ganglia volumes in patients with Gilles de la Tourette syndrome*. Arch Gen Psychiatry. 2003; 60:415-24), (6) 0.95 for the thalamus (see, e.g., Ivanov I, Bansal R, Hao X, Zhu H, Kellendonk C, Miller L, et al. *Morphological Abnormalities of the Thalamus in Youths With Attention Deficit Hyperactivity Disorder*. Am J Psychiatry. 2010; 167:397-408), and (7) 0.98 for cortical thickness (see, e.g., Peterson B S, Warner V, Bansal R, Zhu H, Hao X, Liu J, et al. *Cortical thinning in persons at increased familial risk for major depression*. Proc Natl Acad Sci USA. 2009; 106:6273-8). Region definitions for all participants were reviewed for accuracy by an expert in neuroanatomy (B.S.P.).

Exemplary Quantifying of Local Variation in Surface Morphological Features

Previously described methods (see, e.g., Peterson B S, Warner V, Bansal R, Zhu H, Hao X, Liu J, et al. *Cortical thinning in persons at increased familial risk for major depression*. Proc Natl Acad Sci USA. 2009; 106:6273-8; Peterson B S, Choi H A, Hao X, Amat J, Zhu H, Whiteman R, et al. *Morphology of the Amygdala and Hippocampus in Children and Adults with Tourette Syndrome*. Archives General Psychiatry. 2007; Bansal R, Staib L H, Wang Y, Peterson B S. *ROC-based assessments of 3D cortical surface-matching algorithms*. Neuroimage. 2005; 24:150-62; Peterson B S. *Form Determines Function: New Methods for Identifying the Neuroanatomical Loci of Circuit-Based Disturbances in Childhood Disorders*. Journal of the American Academy of Child and Adolescent Psychiatry. 2010; 49(6):533-5; and Plessen K J, Bansal R, Zhu H, Whiteman R, Quackenbush G A, Hugdahl K, et al. *Hippocampus and amygdala morphology in Attention-Deficit/Hyperactivity Disorder*. Arch Gen Psychiatry. 2006; 63:795-807) can be used, for example, to quantify precisely the local variations in morphological features across the surfaces of the brain regions that can be defined. These methods can permit a finer-grained subdivision of cerebral regions than may be possible using more conventional measures of overall volume, thereby providing greater power to detect localized abnormalities within the region. For example, the cerebrum can be first coregistered to a template brain using a similarity transformation that maximized mutual information across the images. (See, e.g., Viola P, Wells, W. M., editor. *Alignment by Maximization of Mutual Information*. IEEE Proc of the 5th Int Conf on Computer Vision; 1995 June 20-23; Boston, Mass.). Then, a rigid body transformation can be used to coregister individual brain regions to the corresponding template region. Next, each brain region can be wrapped nonlinearly to the corresponding template region using a high-dimensional warping algorithm. (See, e.g., Christensen G E, Rabbitt R D, Miller M I. *3D brain mapping using a deformable neuroanatomy*. Physics in medicine and biology. 1994; 39(3):609-18). Each brain region can be thus warped to the same size and shape as the template region, allowing identification of points on the surface of each region that can corresponded precisely with those of the template region. Then, the Euclidean distance of each point from the corresponding point on the template can be calculated across the entire surface of each region.

These exemplary distances can be, for example, positive in sign for protrusions and negative for indentations relative to the template surface. For any given group of participants, this set of signed Euclidean distances can constitute a smooth random field on the surface of the template region that quantified local variation in surface morphological features of that region for each participant. A single representative brain can be selected as a template rather than an averaged brain because tissue interfaces, such as CSF gray matter or gray-white matter interfaces, are typically well defined in a single brain. In contrast, in an average brain these interfaces are typically blurred, thereby increasing registration errors that are subtle but can be important when distinguishing subtle effects across populations. In addition, precise surface morphometry typically requires smooth surface devoid of topological defects, which can typically be ensured by using a single brain as a template.

The thickness of the cortical mantle can be measured in the brains using a 3-dimensional morphological operator to distance-transform the surface of the white matter to the surface of the cortex. (See, e.g., Haralick R, L. S. *Computer and Robot Vision*, volume 1: Addison-Wesley Publishing Company; 1992; and Lorensen W, Cline H. *Marching Cubes: a High-Resolution 3D surface construction algorithm*. Computer Graphics. 1987; 21:163-9). This operation can calculate the cortical thickness as the smallest distance of each point on the external cortical surface from the outermost surface of the white matter. Because these thicknesses were measured in template space, their values inherently can account for generalized scaling effects in the brain.

Exemplary Conformal Mapping of Local Variations in Brain Measures

Conformal mapping can be used to prepare the surface measures (e.g., Euclidean distances and cortical thickness) for spherical wavelet analyses. The purpose of conformal mapping can be to transfer the surface measures from the template region onto the surface of a unit sphere, while preserving the angles between vectors on the template and spherical surfaces. Because conformal mapping can preserve angles, the shape of a small region on the brain surface can be preserved when it is mapped onto the unit sphere. A Marching Cubes procedure can be used, for example, to extract the surface $\Sigma \subset \mathfrak{R}^3$ of the template region as a triangular mesh. (See, e.g., Lorensen W, Cline H. *Marching Cubes: a High-Resolution 3D surface construction algorithm*. Computer Graphics. 1987; 21:163-9). The extracted surface $\Sigma$ can be embedded into the three dimensional space $\mathcal{R}^3$ and can be assumed to be of genus 0, e.g., the surface can be topologically equivalent to a sphere $S^2$ and preferably does not intersect itself. By removing a single point p from the surface $\Sigma$ and a point p' from the sphere $S^2$, the conformal mapping $z: \Sigma\backslash\{p\} \rightarrow S^2\backslash\{p'\}$ can be estimated by solving the partial differential equation, e.g., $$\Delta z = \left(\frac{\partial}{\partial u} - \frac{\partial}{\partial v}\right)\delta_p,$$

where $\Delta$ can be the Laplace-Beltrami operator, $\delta_p$ can be the Dirac delta function at point p, and u and v can be the conformal coordinates in the neighborhood of the point p. This equation can be solved, for example, using a method for finite element analysis by first mapping the coordinates of the template surface to the coordinates of a plane while preserving the angles between the measures on that surface. (See, e.g., Angenent S, Haker S, Tannenbaum A, Kikinis R. *On the Laplace-Beltrami Operator and Brain Surface Flattening*. IEEE Trans on Medical Imaging. 1999; 18(8):700-11). Next, a stereographic projection can map the coordinates of the plane to the coordinates of the sphere. Those coordinates can be used to transfer the brain measures from the template surface to the corresponding locations on the sphere's surface.

Exemplary Spherical Wavelet Representation

Morphological features can typically be measured at more than 10,000 voxels across the surface of a template region. This number of measures typically precludes the application of clustering techniques to those measures directly because it would typically require a dataset containing many thousands of brains, and even the largest imaging datasets generally contain images from a few hundred participants. Moreover, certain exemplary embodiments of the present disclosure are not directed classifying individual points on the surface, but instead spatial patterns of variation in those measures across the surface. Therefore, before applying clustering techniques to the dataset, the dimensionality of the dataset is first preferably reduced in a manner that can capture that spatial pattern in variation of the measures. This can be accomplished, for example, by applying a spherical wavelet transform to those measures when conformally mapped onto the unit sphere. This exemplary wavelet transform can generate the scaling coefficients that can encode the spatial variation in the measures on the unit sphere at varying degrees of spatial resolution.

Because wavelets typically have local support—e.g., they equal zero outside a small region—in both the spatial and frequency domains, they can be used to represent functions at multiple levels of spatial detail. A wavelet transform, through dyadic translations and dilations of a mother wavelet and scaling function, can generate coefficients for a function such that only a small subset of the coefficients can represent the function with a high degree of precision, thereby permitting compression and efficient processing of imaging data. The wavelet function, e.g., $\psi_{j,k}$ and the scaling, e.g., $\varphi_{j,k}$, at a resolution, e.g., j and an index, e.g., $k \in K(j)$ (K(j) can be a set of integers at resolution j indexing the position of the wavelet and scaling function), can be a linear combination of the scaling functions $\varphi_{j+1,k}$ at the higher resolution j+1. Therefore, the wavelet and scaling functions can be self-similar at differing spatial resolutions. If $L_2(S^2, d\omega)$ is the space of all scalar functions having finite energy over the sphere $S^2$, a multi-resolution analysis can generate a sequence of closed subspaces $V_j \subset L_2$, $\forall j \geq 0$, such that: (1) $V_j \subset V_{j+1}$, that can be $$\varphi_{j,k} = \sum_l h_{j,k,l}\varphi_{j+1,l}, \qquad (2)$$

$\cup_{j\geq 0} U_j$ can be dense in $L_2$, and (3) the set of scaling functions $\{\varphi_{j,k}|k\in K(j)\}$ can be a Riesz basis of $V_j$. The wavelet functions $\psi'_{j,k}$ can form the bases of the difference space $W_j$ between two successive levels of representation, that can be $V_j \oplus W_j = V_{j+1}$. In addition to local support, the wavelet functions can have vanishing moments: For example, if wavelets $\psi_{j,k}$ have N vanishing moments, then there can exist N independent polynomials $P_i$, $0 \leq i \leq N$ such that $\langle \psi_{j,k}, P_i \rangle = 0$, for all $j \geq 0$, $m \in M(j)$, where $M(j) \subset K(j+1)$ can be an index set.

Historically, wavelet transforms can be initially limited to infinite R" spaces (41), but they subsequently can be extended to finite R" spaces. (See, e.g., Cohen A, Daubechies I, Jawerth B, Vial P. *Multiresolution analysis, wavelets and fast algorithms on an interval*. CR Acad Sci Paris Ser I Math I. 1993; 316:417-21). More recently, they have been extended to analyze scalar functions defined on a sphere using lifting schemes. (See, e.g., Schroder P, Sweldens W. *Spherical Wavelets: Efficiently Representing Function on the Sphere. Proceedings of the 22nd annual conference on Computer graphics and interactive techniques* 1995:161-72; and Sweldens W. *The lifting scheme: A custom design construction of biorthogonal wavelets*. Department of Mathematics, University of South Carolina, 1994 Contract No.: Tech. Rep. 1994:7). A lifting scheme can build biorthogonal wavelets that can be smoother and that can have more vanishing moments than do simple scaling and wavelet functions. A forward analysis of a spherical wavelet transform can begin computing coefficients for a function at the highest spatial resolution, continuing until it reaches the lowest possible spatial resolution. At each resolution, unlifted wavelet coefficients can be computed, and then these coefficients can be lifted to compute the wavelet coefficients, e.g., $\gamma_{j,k}$, and the scaling coefficients, e.g., $\lambda_{j,k}$. Synthesis, or the inverse transform, in contrast, can begin by computing the coefficients at the lowest resolution and ends at the function with the highest resolution. Two differing methods of wavelet analyses can be used to determine or compute scaling coefficients for the surface measures, for example: (1) the linear lifted method, which can use information from the two nearest neighbors $K(j)=\{v_1, v_2\}$ at a location on the mesh of the unit sphere to interpolate the transformation, and (2) the lifted butterfly method, which can use information from the eight neighbors $K(j)=\{v_1, v_2, f_1, f_2, e_1, e_2, e_3, e_4\}$ on the mesh of the sphere to compute the scaling coefficients. (See, e.g., FIG. 5).

Exemplary Discovery of Natural Groupings Using Hierarchical Clustering

Hierarchical clustering can be a powerful, unsupervised procedure for discovering natural structure within a dataset, especially when the groupings of data are unknown a priori. Research in the clinical neurosciences increasingly indicates that the diagnostic categories based upon descriptive diagnostic systems from reports of symptoms typically do not align with the underlying neurobiology of those disorders. Groupings of brains that are generated from clinical diagnoses alone therefore can frequently misclassify brains if their features do not map tightly to a clinical diagnosis, especially, for example, when disturbances affect neural pathways that can be common across disorders. To reduce these classification errors, exemplary hierarchical clustering procedures can be used to discover naturalistic groupings of brain features, and then diagnostic labels can be assigned to those groupings of brains using the known clinical diagnoses for the persons whose brains constituted the majority of each group. Those groupings and labels can then be used, for example, to classify new brains from a separate dataset. Thus, although the features that can generate the classification procedure can be defined by the clinical diagnoses, hierarchical clustering can generate groupings based solely on the morphological features and therefore the brains from participants can be clustered in groups that, for example, shared similar morphological features.

An exemplary method for hierarchical clustering according to the present disclosure can generate a sequence of clusters that partitions an imaging dataset from n participants, e.g., using a measure of dissimilarity between any two groups of features vectors. For example, starting with n clusters at level 1, with each cluster containing data from one participant, the dataset can be partitioned into n−1 clusters at level 2, n−2 clusters at level 3, and so on, such that one cluster can be present at level n. In this sequence of clusterings, any two feature vectors x and x' can be grouped into one cluster at some level, and they can remain together at the higher levels. Furthermore, dissimilarity between two clusters can increase with increasing levels, and therefore the groupings of feature vectors that can be generated by hierarchical clustering can be visualized at various levels using a nonintersecting, binary tree, for example, such as a dendrogram. An exemplary dendrogram can be drawn to scale to show the dissimilarity between the groups of feature vectors and to help identify natural groupings within the dataset. An unusually large difference in the similarity values across levels may indicate a natural clustering at the lower level. If the similarity values for various levels were evenly distributed across the range of possible values, however, then no particular clustering can be more natural than any other.

The use of exemplary hierarchical clustering procedures to generate a correct natural grouping of participants can depend on the similarity measure used to compare feature vectors, as well as on the method that groups these features using those similarity measures. The similarity between features (e.g., sets of scaling factors) can be defined as either the Euclidean distance for the feature vectors encoding local variations in the surface morphological measures of a single brain region, or the standardized Euclidean distance for the feature vectors encoding local variations in the surfaces from multiple brain regions. For example, either the average linkage or Ward's linkage can be used on the similarity measures to group the feature vectors. The average linkage can calculate the average of the distances between pairs of feature vectors in the two clusters and then merged as level k the two groups that had the smallest distance between averages. In other words, the average distance $d_{ave}(D_i, D_j)$ between clusters $D_i$ and $D_j$ can be computed as, e.g.:

$$d_{ave}(D_i, D_j) = \frac{1}{|D_i||D_j|} \sum_{x \in D_i, x' \in D_j} \|x - x'\|$$

Ward's linkage, in contrast, can calculate the distance between two clusters $D_i$ and $D_j$ as the increase in the error sum of squares (ESS) of the new cluster $D_{ij} = D_i \cup D_j$, obtained as the union of the individual clusters. For example, for a cluster $D_i$, the $ESS(D_i)$ can be computed as, e.g.:

$$ESS(D_i) = \sum_{x \in D_i} \left\| x - \frac{1}{|D_i|} \sum_{y \in D_i} y \right\|^2$$

and therefore Ward's distance $d_{ward}(D_i, D_j)$ can be computed as e.g.:

$$d_{ward}(D_i, D_j) = ESS(D_{ij}) - [ESS(D_i) + ESS(D_j)].$$

Ward's linkage therefore can generate cohesive groupings of participants by minimizing the increase in within-group variance at each level.

Exemplary Controlling for Nuisance Variables

Brain measures may differ because of differing ages, gender composition, or whole brain volume (WBV) across individuals, in addition to differences caused by pathological processes in neuropsychiatric illnesses. To ensure that the exemplary method can generate naturalistic groupings that generally represent the underlying pathological processes, the method of hierarchical clustering can be applied to brain measures that can be corrected for age, gender, and WBV. The brain measures can be determined or computed on brains that can be normalized into the coordinate space of a template brain of a healthy individual, and therefore they can be corrected for differing WBV across individuals. These brain measures can be further corrected for age and gender effects by applying linear regression with age and gender as the independent variables and brain measure as the dependent variable. The regression analysis generated residual brain measures that can be subsequently clustered to generate groupings that represented the underlying pathological processes in the brain.

Exemplary Quantitative Evaluation of Groupings

If a dataset can indeed be clustered into natural groupings, then the distances between groups should typically be larger than the distances between participants within groups. These exemplary distances can be compared using the exemplary hierarchical clustering procedure by computing the Cophenetic Correlation Coefficient (CPCC), e.g., the coefficient for the correlation of the distance between any two feature vectors $(x_1, x_2)$ with the distance between the two clusters $(C_1, C_2)$ that were merged when those two feature vectors were first placed in the same cluster. The possible values of the CPCC can range from −1 to 1, with larger positive values indicating a good match between the data values and the hierarchy generated in the clustering procedure.

Exemplary Quantifying Performance of the Diagnostic Classification

Because exemplary hierarchical clustering and other clustering methods typically generate groupings even if feature vectors are distributed randomly in the feature space, groupings are preferably assessed for their validity and reproducibility. Therefore, the performance and reproducibility of the exemplary classification procedures can be quantified using, for example, a leave-one-out (LOO) and split-half cross validation analysis to compute misclassification rates. The misclassification rates can be computed, for example, as the proportion of false negatives (FN) to the sum of true positives (TP) and FN $$\left( e.g., \frac{FN}{TP + FN} \right),$$

and the proportion of false positives (FP) to the sum of true negatives (TN) and FP $$\left(\text{e.g., } \frac{FP}{FP+TN}\right).$$

Exemplary cross validation methods can distinguish the data that can be used to learn the classification model and the data that can be used to test classification performance of the model. For example, split-half analyses that can use a random half of the dataset to learn the model and the other half to assess the model's classification accuracy. Cross-validation procedures can determine or compute the prediction error of the model in three steps, e.g.: (1) the N feature vectors can be divided into n=N/k sets. For leave-one-out cross validation, k=1—e.g., each set initially can contain one feature vector. (2) One of the n sets can be selected as the test dataset, and hierarchical clustering can be applied to feature vectors for brains in the remaining n−1 sets to generate groupings. These groupings and the test data can be then used to compute the prediction error (PE). A diagnostic label can be assigned to each group using majority rule (e.g., the clinical diagnosis that the majority of participants carried within each natural grouping can become the label assigned provisionally to the participants within that group; the accuracy of that assignment was assessed subsequently). The method can accurately classify the test participant if that person's known clinical diagnosis can be the same as the diagnosis assigned to the group; otherwise, the participant can be regarded as misclassified. (3) Step 2 can be repeated for each of the n sets of data, with the n estimates of the prediction error combined to calculate an overall estimate of PE. The number of participants can be counted who were misclassified for each diagnosis and the average misclassification rate for each diagnosis can be computed by dividing the number of participants who carried that diagnosis and who were misclassified by the total number of participants who had that clinical diagnosis as judged by the consensus diagnostic procedures performed by senior clinicians.

Split-half analyses, in contrast, can possibly parallel the real-world application in which one set of brains and clinical diagnoses can be used to generate the learned classification procedure and another independent set of brains can be classified using such previously generated procedure. The performance of the exemplary procedure can be then assessed using the accuracy of classification of the new independent set of brains. Split-half analysis can also be applied to assess the validity of the groupings generated by the exemplary classification procedure. The misclassification rates for a split-half analysis can be stochastic because, for example, for a set of N=2 M feature vectors, they can be computed from any one of the $$\binom{N}{M} = \prod_{i=1}^{M}\left(\frac{N-M+i}{i}\right)$$

pairs of training and test subsets, with each pair of training and test subset typically generating different estimates for the misclassification rates. For a small number N of feature vectors in the entire cohort, the misclassification rates computed by both split-half and LOO analyses can vary across the pair of training and test subsets of the dataset. To assess the stability of the misclassification rates and to evaluate that the average misclassification rates can be similar for the two analyses in the cohort of participants, each cohort can be subdivided into 10 pairs of test and training subsets, with distinct feature vectors randomly selected from the original set of vectors. To each of these 10 pairs of test and training subsets, split-half analysis can be applied thereby enabling estimation of an average and standard deviation of the misclassification rates. In addition, an exemplary LOO analysis can be applied independently to the 10 test and 10 training subsets, and an average and standard deviation of the rates computed by LOO analysis can be computed.

The misclassification rates determine and/or computed using split-half analysis can be expected to be more conservative estimates than those computed using the LOO analysis. However, split-half analyses for each diagnostic classification using N feature vectors for training set is typically not possible if only one set of N feature vectors is used. Therefore, to determine and/or compute split-half estimates for a training set with N feature vectors, the difference in the split-half and LOO rates computed for the 10 pairs of test and training datasets can be computed, and this difference can be added to those determined and/or computed using the exemplary LOO analysis of the entire cohort to determine and/or calculate the adjusted misclassification rates. These exemplary adjusted rates can generalize better in a real-world application and therefore can be used to compute the sensitivity $$\left(\frac{TP}{TP+FN}\right),$$

specificity $$\left(\frac{TN}{TN+FP}\right),$$

and positive predictive value $$\left(PPV = \frac{TP}{TP+FP}\right)$$

of the exemplary procedures to diagnose neuropsychiatric illnesses automatically and without human intervention.

Exemplary Validation Using Computer-Generated Datasets

A plurality (e.g., two) synthetic datasets can be generated, each with increasing levels of complexity in their surface morphologies, by superimposing spherical indentations or protrusions of known size positioned precisely in the dorsolateral prefrontal cortex (DLPFC) or occipital cortex (OC). (See, e.g., Bansal R, Staib L H, Wang Y, Peterson B S. *ROC-based assessments of 3D cortical surface-matching algorithms.* Neuroimage. 2005; 24:150-62). These two datasets can be used to assess the construct validity of the exemplary procedures. The deformation in DLPFC can be centered in the midportion of the pars triangular is over the inferior frontal gyms. The deformation in OC can be placed to the left of the interhemispheric fissure on the lowermost portion of the occipital lobe, such that the deformation can be tangential both to the cistern immediately superior to the cerebellum and the interhemispheric fissure. The accuracy of the placement of these deformations can be confirmed by viewing the deformed brains in the coronal, axial, and sagittal planes. The first dataset can be created, for example, from copies of a single brain, and the second dataset can be created, for example, from the brains of 20 different individuals. The second dataset can be used to determine the optimal resolution of the scaling coefficients that best discriminate brains of healthy individuals from those with neuropsychiatric illnesses.

Synthetic Datasets Constructed from a Single Brain

To create the first exemplary set of 10 brains, $S_{DI}^1$, a deformed brain can be generated by adding a 15 mm indentation in the DLPFC in a copy of $s^1$, and 10 copies of that brain can be placed, each with a differing amounts of translations and rotations, in the coordinate space of the template brain. (See, e.g., FIGS. 6 and 7). Similarly, for the second exemplary set of 10 brains, $S_{DP}^2$, a deformed brain can first be generated by adding a 15 mm protrusion to the same location of the DLPFC in a copy of $s^1$, and then 10 copies of that same brain can be placed at 10 random locations in the coordinate space. Using identical procedures, a third set $S_{OI}^3$, and a fourth set $S_{OP}^4$ of 10 images can be generated, for example, by adding an indentation and a protrusion, respectively, in the OC region in the copies of $s^1$ and then placing them at 10 random locations in the space. From these four sets of deformed brains, three new sets can be generated, e.g.: (1) $S_{DIP} = S_{DI}^1 \cup S_{DP}^2$ of 20 brains, (2) $S_{OIP} = S_{OI}^3 \cup S_{OP}^4$ of 20 brains, and (3) $S_{DOIP} = S_{DI}^1 \cup S_{DP}^2 \cup S_{OI}^3 \cup S_{OP}^4$ of 40 deformed brains. The exemplary wavelet transform and classification procedures can be applied to discover natural groupings in each of these three synthetic datasets. Because brains in these datasets can be identical to $s^1$, except for the added protrusion and indentation, the brains can be expected to be clustered into four groups, e.g.: one with protrusions in the DLPFC, a second with indentations in the DLPFC, a third with protrusions in the OC, and a fourth group with indentations in the OC. (See, e.g., FIGS. 6 and 7).

Exemplary Synthetic Datasets Constructed from Different Individuals

From the brains of 20 healthy individuals, $\{s^1, s^2, \ldots, s_{20}\}$, 4 sets of synthetic data can be generated, e.g.: (1) the first set $D_{DI}^1 = \{S_{DI}^1, s_{DI}^2, \ldots, s_{DI}^{20}\}$ of 20 deformed brains can contain a 15 mm indentation in the DLPFC, (2) the second set $D_{DP}^2\{s_{DP}^1, s_{DP}^2, \ldots, s_{DP}^{20}\}$ of 20 brains can contain a 15 mm protrusion in the DLPFC, (3) the third set $D_{OI}^3 = \{s_{OI}^1, s_{OI}^2, \ldots, s_{OI}^{20}\}$ brains can contain a 15 mm indentation in the OC, and (4) the fourth set $D_{OP}^4 = \{s_{OP}^1, s_{OP}^2, \ldots, s_{OP}^{20}\}$ of 20 brains can contain a 15 mm protrusion in the OC. From these sets of synthetic data, 3 new subsets of brains can be created, e.g.: (1) the first subset $D_{DIP} = \{s_{DI}^1, \ldots, s_{DI}^{10}, s_{DP}^{11}, \ldots, s_{DP}^{20}\}$ can contain 10 brains with indentations and another 10 brains with protrusions in the DLPFC, (2) the second subset $D_{OIP} = \{s_{OI}^1, \ldots, s_{OI}^{10}, s_{OP}^{11}, \ldots s_{OP}^{20}\}$ of 10 brains with indentations and another 10 brains with protrusions in the OC, and (3) the third subset $D_{DOIP} = \{s_{DI}^1, \ldots, s_{DI}^{10}, s_{DP}^{11}, \ldots s_{DP}^{20}\}$ of 10 brains with indentations at DLPFC, another 10 brains with protrusion in the DLPFC, 10 more brains with indentations in the OC, and yet another 10 brains with protrusions in the OC. The exemplary method can be applied to automatically discover the natural groupings within these three sets of brains. For each of the two sets $D_{DIP}$, and $D_{OIP}$, the brains can be expected to cluster into two groups: one with indentations and the other with protrusions. Brains from the set $D_{DOIP}$ can be expected to cluster into four groups, one with protrusions in the DLPFC, another with indentations in the DLPFC, another with protrusions in the OC, and a last one with indentations in the OC.

Exemplary Validation Using Real-World Data and Gold-Standard Clinical Diagnoses

The natural groupings identified in the exemplary classification procedure can be validated using surface morphological measures in a large group of healthy individuals and groups of persons who had known clinical diagnoses established by senior clinicians. The exemplary classification scheme can be applied to the scaling coefficients that can be determined differed at high levels of statistical significance (e.g., p-values<$10^{-7}$) between persons with a specific neuropsychiatric disorder and healthy comparison persons. The p-value for the statistical significance can be determined empirically by first applying LOO analysis to scaling coefficients that differed at decreasing p-values and then selecting the p-value associated with the lowest misclassification rates. (See FIG. 8). Using feature vectors that differed at this stringent statistical threshold can both reduce the dimensionality of the feature space and identify the features that best discriminated feature vectors for brains in each of the two groups. Each group of brains that hierarchical clustering can generate can be assigned the diagnosis of the majority of participants contained in that group. Furthermore, although the feature vectors upon which hierarchical clustering was performed can be empirically selected, that selection can be subsequently validated and their reproducibility can be assessed using split-half cross validation. The selected feature vectors therefore can typically generalize to other similar datasets.

Feature vectors can be determined and/or computed from several brain regions, according to the availability of their manual tracings. For discriminating brains of individuals with either TS or ADHD from those of healthy comparison individuals and for discriminating TS children from ADHD children, feature vectors computed from 7 brain regions (e.g., the cortical surface, globus palladus, putamen, caudate, thalamus, amygdala, and hippocampus) can be used in each hemisphere, whereas for discriminating brains between persons with other clinical diagnoses feature vectors computed from 3 brain regions (e.g., the cortical surface, amygdala, and hippocampus) can be used in each hemisphere. For the brains of individuals who were at either high or low risk for depression, feature vectors computed from the cortical thickness can be used. The exemplary classification procedures can be applied to discriminate, e.g., (a) 41 children with ADHD from 42 healthy children, (b) 71 children with TS from 41 children with ADHD, (c) 26 adults with BD from 40 healthy adults, (d) 65 adults with schizophrenia (SZ) from 36 TS adults, (e) 65 adults with SZ from 26 BD adults, (f) 65 adults with SZ from 40 healthy adults, (g) 36 adults with TS from 40 healthy adults, (h) 71 children with TS from 42 healthy children, (i) 65 adults with SZ, 36 adults with TS, and 40 healthy adults, and (j) 65 adults with SZ, 26 adults with BD, and 40 healthy adults. (See FIG. 8).

Exemplary Identification of Persons at High or Low Familial Risk for Developing a Disorder Individuals who were at either high familial risk (HR) or low familial risk (LR) for developing Major Depressive Disorder (MDD) can be classified. The group can include, for example, 66 HR and 65 LR individuals. Previously, the presence of a thinning of the cortical mantle in the lateral aspect of the right cerebral hemisphere and mesial wall of the left hemisphere of the HR compared with LR participants has been shown. (See, e.g., Peterson B S, Warner V, Bansal R, Zhu H, Hao X, Liu J, et al. *Cortical thinning in persons at increased familial risk for major depression*. Proc Natl Acad Sci USA. 2009; 106:6273-8). The cortical thinning can be present even in those HR individuals who had never been ill with MDD. Therefore, scaling coefficients for local variations in cortical thickness of the HR and LR participants can be computed. Classification can be more challenging in these high and low risk groups than in groups of already-affected people because most of the HR and LR participants had no lifetime history of MDD, some of the LR participants in generation 3 had parents with prior depression who married into the cohort, and some of the members of the LR group did have a lifetime history of MDD. Therefore, at least some of the participants in these two risk groups can be expected to have similar brain features, and misclassification of at least some participants in the HR group as being in the LR group, and vice versa can be expected.

Exemplary Results

Exemplary Synthetic Datasets

Exemplary Synthetic Datasets Constructed from a Single Brain

In an exemplary dataset with 40 brains with indentations and protrusions in both the DLPFC or OC, the exemplary method can correctly cluster the brains into 4 groups of 10 brains each, one with protrusions in the DLPFC, another with indentations in the DLPFC, a third group with protrusions in the OC, and a last group with indentations in the OC. (See, e.g., FIG. 9). Classification rates can be perfect for this synthetic dataset.

Additionally, the same groupings can be generated when using either a lifted interpolate or a lifted butterfly wavelet and when using either an Average or a Ward's linkage measure of distance. The analysis using the lifted interpolate wavelet and the Ward's linkage distance, however, can generate more coherent and better separated groups. (See, e.g., FIG. 9). Thus, in subsequent analyses, the lifted interpolate wavelet can be used to compute scaling coefficients and Ward's linkage to generate optimal groupings in hierarchical clustering.

Exemplary Synthetic Datasets Constructed from Different Individuals

Using scaling coefficients at a higher resolution of the wavelet analyses, the exemplary method can generate groups of brains with indentations in the DLPFC, protrusions in the DLPFC, indentations in the OC, and protrusions in the OC. (See, e.g., FIG. 10). At lower resolution, the performance of classification can be poor when using datasets constructed from different individuals because differing surface morphology across individuals differentially affected the added deformations. The scaling coefficients at the lower resolution therefore can encode both the inherent variation in surface morphology in these individuals and the added deformations, and therefore the groupings generated by the exemplary method can be guided by variation in surface morphological features in these individuals. At higher resolutions (e.g., at smaller spatial extents across the cortical surface), the effects of the variation in surface morphology can be smaller in the scaling coefficients computed across individuals; the scaling coefficients at the higher resolution therefore can encode more accurately the deformation added to the surfaces of these brains. Thus, scaling coefficients computed at the higher resolution can be used for classifying individuals subsequently in the exemplary analyses of real-world datasets.

Exemplary Datasets of Persons with Neuropsychiatric Illnesses

Cophenetic Correlation Coefficient

A measure of the correlation between the separation of the naturalistic groupings identified for the exemplary datasets and the Euclidean distances between the feature vectors, termed the Cophenetic Correlation Coefficient (CPCC), can be consistently high (e.g., near 0.7) for the clustering of data generated using Ward's linkage. It can be noted, however, that the CPCC can be sensitive to the linkage method used to form the hierarchy and is therefore not necessarily an ideal metric. (See, e.g., Holgersson M. *The limited value of cophenetic correlation as a clustering criterion Pattern Recognition.* 1979; 10(4):287-95; and Rohlf F J. *Adaptive hierarchical clustering schemes.* Systematic Zool. 1970; 19:58-82). Visual inspection of the distances between groups and between participants within groups using dendrograms (see, e.g., FIGS. 5-8) and the high CPCC values suggested that the naturalistic groupings were typically valid.

Exemplary Three-Way Classifications Using Real-World Data and Gold-Standard Clinical Diagnoses In contrast to the two-way classifications, the performance of the exemplary method for three-way classifications can be poor: In discriminating the brains of SZ adults, BD adults, and healthy adults (HA), for example, the adjusted misclassification rates can be, for example, 0.80, 0.83, and 0.046, for SZ adults, BD adults, and HA, respectively. (See, e.g., FIG. 11, left). However, the brains of SZ adults, BD adults, and HA can be accurately discriminated by applying an iterative, two-way classification strategy in which the brains of HA can be discriminated from those of a combined group of SZ adults and BD adults, and a different set of feature vectors can be applied to discriminate the brains of SZ adults from BD adults. (See, e.g., FIG. 2). Because the brains of SZ adults can be discriminated from those of BD adults, the misclassification rates for the iterative approach can be, for example, 0 for HA, 0.14 for BD adult, and 0.14 for SZ adult. Similarly, an iterative, two-way classification strategy can be best for discriminating the brains of SZ adults, TS adults, and HA (See, e.g., FIG. 11, right): the brains of SZ adults can first be discriminated from those of a combined group of TS adults and HA, and then a different set of features can be used to discriminate the brains of TS adults from HA. (See, e.g., FIG. 3). The misclassification rates for this iterative approach can be, for example, 0.10 for HA, 0.168 for TS adult, and 0.0245 for SZ adult. (See, e.g., FIG. 11).

Diagnosing individuals using brain imaging measures alone can have the potential to transform the clinical care and research of neuropsychiatric illnesses. Imaging-based diagnoses can be helpful at the stage of initial diagnosis, when symptoms frequently overlap across disorders and create diagnostic confusion. Discriminating Bipolar Disorder from Schizophrenia, or ADHD from healthy children, for example, is often difficult in the early stages of these illnesses, and the exemplary classification procedure can identify these diagnostic groups with accuracy. Accurate initial diagnoses can potentially reduce the cost and morbidity associated with the initiation of incorrect treatments based on an incorrect initial diagnosis. Imaging-based classifications in persons who are at increased risk for developing a neuropsychiatric illness can likely facilitate the development of primary or secondary prevention strategies for that illness, the feasibility of which can be demonstrated by discriminating individuals at high or low risk for familial MDD, even in those who have not yet manifested overt symptoms of the illness. Additionally, the same classification techniques that can be used to discriminate two diagnoses can in principle be used to identify brain-based subtypes within a single clinical diagnosis, which if successful can help to predict the future course of illness and to develop individualized treatments for each biological subtype. Finally, brain-based diagnoses and the identification of biological subtypes can reduce the presence of phenocopies that can be detrimental to the discovery of the genes that cause neuropsychiatric illnesses.

FIG. 1 shows an illustration of exemplary classifications of a child as healthy or with ADHD and as having either TS or ADHD using certain exemplary embodiments of the present disclosure. The exemplary acronyms shown in FIG. 1 are provided as follows: GP, globus pallidus, CN, caudate nucleus; PUT, putamen; TH, thalamus; AMY, amygdala; HC, hippocampus; A: Anterior; P: Posterior. In the exemplary cohort of 42 healthy children (HC), 41 ADHD children, and 71 children with TS, the scaling coefficients can be computed for the left and right globus pallidus, putamina, caudate nuclei, thalami, amygdalae, and hippocampi. Then, hierarchical clustering can be independently applied to those coefficients that differed significantly (e.g., P-value<$10^{-7}$) between: (1) ADHD children and HC, and (2) TS children and ADHD children. The left dendrogram can suggest the presence of two groups: one (labeled as HC) which can include 36 healthy children, and the other (labeled as ADHD children) which can include 41 ADHD children and 6 healthy children. The right dendrogram can indicate that the brains can be clustered into two distinct groups: one labeled TS which included TS children and the other labeled ADHD which included ADHD children. The adjusted misclassification rates (Table 1) can be, for example: 11.5% for healthy children and 6.4% for ADHD children; and 0.17% for TS children and 0.5% ADHD children. Therefore, the sensitivity and specificity can be, for example: 93.6% and 89.5%, respectively, for classifying a child as an ADHD child; and 99.83% and 99.5%, respectively, for classifying a child as having either ADHD or TS. As shown in FIG. 1, the patterns of surface features across the various brain regions that best classified a child can be plotted.

As shown in the graph on the left side of FIG. 1, the patterns that discriminated ADHD child from healthy child can be localized to, e.g.: lateral and posterior portions of the right putamen; anterior portions of the left and medial portion of the right globus pallidus; ventral portion of the left caudate; posterior and medial portions of the left thalamus; ventral portion of the left amygdala, and anterior and posterior portions of the right amygdala; and posterior portion of the left hippocampus. In bright section (102a) are regions with local protrusions, and in darker sections (104a) are regions with local indentations in ADHD children compared with the healthy children.

As shown in the illustration on the right side of FIG. 1, the pattern of surface features that can discriminate between children with TS or ADHD can include: anterior, lateral, and dorsal portions of the left globus pallidus, and dorsal, lateral, and medial portions of the right globus pallidus; ventral portion of the left caudate; dorso-medial portions of the left putamen, and lateral, dorsal, and medial portions of the right putamen; dorsal, posterior, and medial portions of the left thalamus, and posterior portion of the right thalamus; dorsal and posterior portions of the left amygdale, and anterior and posterior portions of the right amygdala; anterior and medial portions of the left hippocampus, and lateral portions of the right hippocampus. Regions in bright sections (102b) are local protrusions, and regions in darker sections (104b) are local indentations, in TS children compared with ADHD children.

Figure 2:
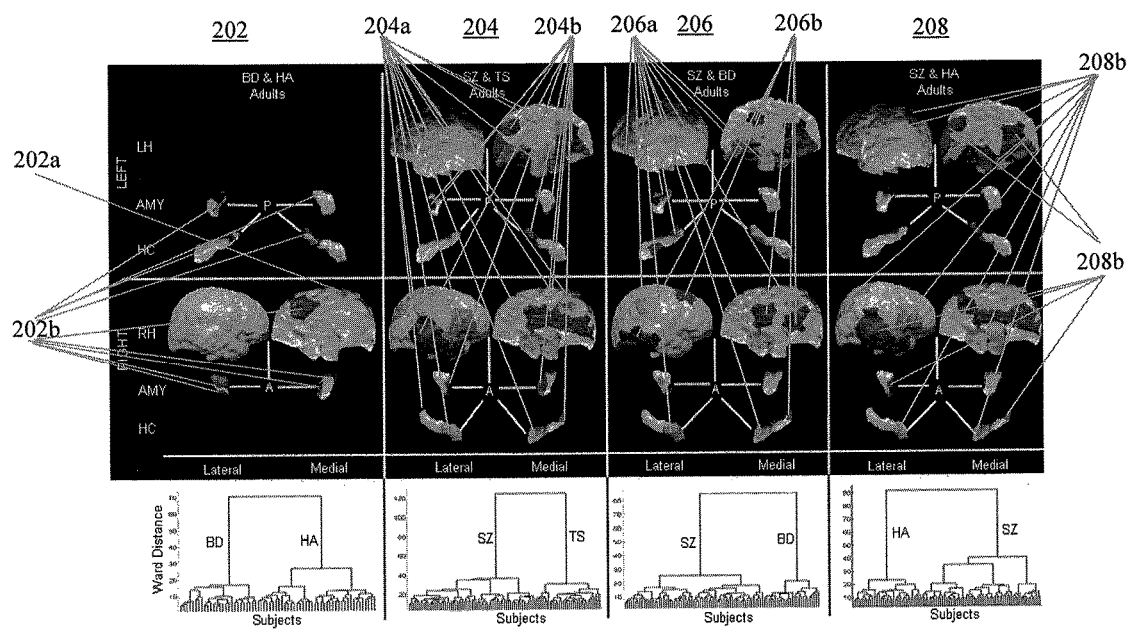
FIG. 2 is an illustration of exemplary classifications of an adult as healthy or with a disorder and between two neuropsychiatric illnesses using certain exemplary embodiments of the present disclosure.

FIG. 2 shows an illustration of exemplary classifications of an adult as healthy or with a disorder and between two neuropsychiatric illnesses using certain exemplary embodiments of the present disclosure. The acronyms shown in FIG. 2 are as follows: LH, left hemisphere; RH, right hemisphere; AMY, amygdala; HC, hippocampus; A, anterior; P, posterior. In the exemplary cohort of 40 healthy adults (HA), 26 bipolar (BD) adults, 36 TS adults, and 65 adults with schizophrenia (SZ), scaling coefficients can first be computed for the left and right hemispheres, amygdalae, and hippocampi. Hierarchical clustering can then be applied independently to those coefficients that differed significantly (e.g., P-value<$10^{-7}$) between: (1) BD adults and healthy adults (1st column—202), (2) SZ adults and TS adults (2nd column—204), (3) SZ adults and BD adults (3rd column—206), and (4) SZ adults and HA (4th column—208). The first exemplary dendrogram can indicate the presence of two groups, e.g.: one (labeled as HA) can include the 40 healthy adults, and the other (labeled as BD adults) can include the 26 BD adults. The second exemplary dendrogram can demonstrate that the brains were clustered into two distinct groups, e.g.: one containing TS adults and the other SZ adults. The third dendrogram also can include two distinct groups, one group of BD adults and the other group of SZ adults. The fourth dendrogram can show two groups of the brains, one labeled healthy adults can include of healthy adults, and the other labeled SZ can include SZ adults and two healthy adults. The adjusted misclassification rates can be, for example: (1) 3.6% for HA and 0% for BD adults, (2) 0% for both the TS and SZ adults, (3) 0% for both the BD and SZ adults, and (4) 6.9% for SZ adults and 5.5% for healthy adults. Therefore, the sensitivity and specificity were (1) 100% and 96.4%, respectively, for classifying a participant as a BD adult, (2) 100% for classifying an adult as TS or SZ adult, (3) 100% for classifying an adult as BD or SZ adult, and (4) 93.1% and 94.5%, respectively, for classifying a participant as SZ adult. The patterns of surface features can be plotted across the various brain regions that best classified an adult.

As shown in the first (from the left) column (202) of FIG. 2, these patterns can be localized to, e.g.: anterior and lateral regions of the left amygdala, and dorsal, lateral, and posterior regions of the right amygdala; posterior regions of the left hippocampus; and dorso-medial regions of the right hemisphere. In a bright section (202a) are regions with local protrusions, and in a dark section (202b) are regions with local indentations in BD adults compared with the healthy adults.

As shown in the second column (204) of FIG. 2, the pattern of exemplary surface features that discriminated between groups can include, e.g.: anterior and medial portions of the left amygdala, and lateral and posterior regions of the right amygdala; anterior and lateral aspects of the left hippocampus, and posterior portion of the right hippocampus; and dorsolateral prefrontal, parietal, and medial regions of the left hemisphere, and dorsolateral prefrontal, temporal, medial, and parietal regions of the right hemisphere. Regions in a bright section (202a) are local protrusions, and regions in a dark section (202b) are local indentations, in SZ adults compared with TS adults.

As shown in the third column (206) of FIG. 2, the pattern of exemplary surface features that discriminated between groups can include, e.g.: dorso-medial portions of the left amygdala, and ventro-medial regions of the right amygdala; posterior and lateral aspects of the left hippocampus, and anterior and posterior portion of the right hippocampus; medial dorso-lateral prefrontal, and parietal regions of the left hemisphere, and ventro-posterior, medial, and posterior lateral regions of the right hemisphere. Regions in a bright section (204a) are local protrusions, and regions in a dark section (204b) are local indentations, in SZ adults compared with BD adults.

As shown in the fourth column (208) of FIG. 2, the exemplary surface features that can discriminate SZ adults from healthy adults can be localized to, e.g.: dorsolateral prefrontal cortex, superior parietal, and medial regions of the left hemisphere, and temporal, occipital, dorso-lateral, and medial regions of the right hemisphere; dorsal regions of left amygdala, and anterior regions of right amygdala; posterior regions of the left hippocampus, and anterior and posterior regions of the right hippocampus. In a bright section (208a) are regions with local protrusions, and in a dark section (208b) are regions with local indentations in SZ adults compared with the healthy adults.

Figure 3:
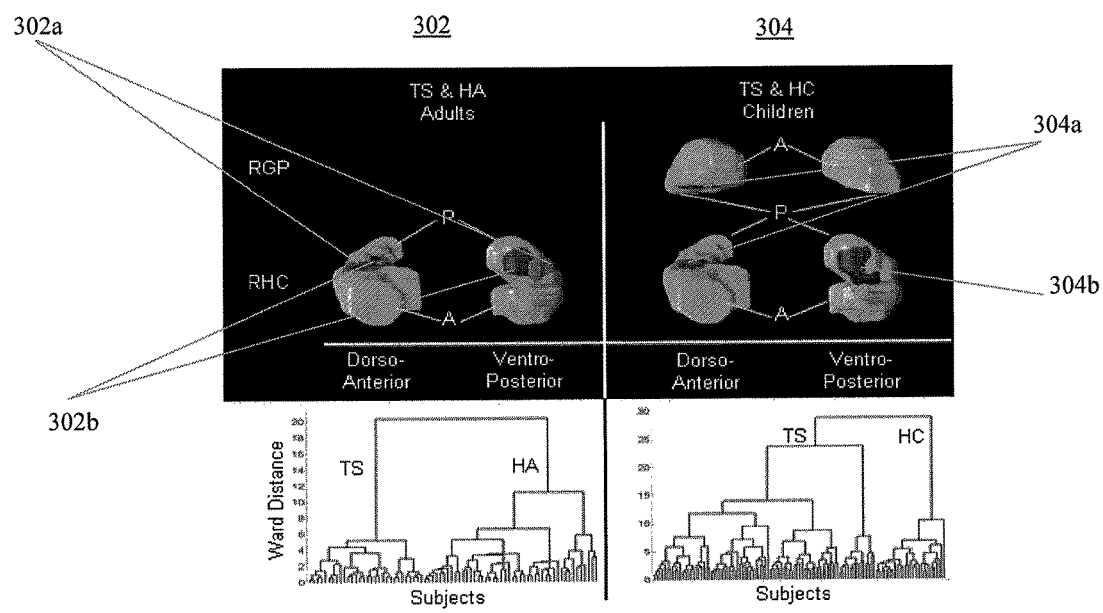
FIG. 3 is an illustration of exemplary classifications of an adult as healthy or with TS using certain exemplary embodiments of the present disclosure.

FIG. 3 shows an illustration of exemplary classifications of an adult as healthy or with TS using certain exemplary embodiments of the present disclosure. The acronyms shown in FIG. 3 are as follows: RGP, Right Globus Pallidus; RHC, Right Hippocampus; A: anterior; P: posterior. In 42 healthy children (HC), 40 healthy adults (HA), 71 children with TS, and 36 adults with TS, hierarchical clustering can independently be applied to scaling coefficients that can differ significantly (e.g., P-value<$10^{-7}$) between (1) adults with TS and healthy adults (left—302), and (2) children with TS and healthy children (right—304). The two largest groups in the right dendrogram can be labeled HC (e.g., this group can include 27 healthy children) or TS children (e.g., this group can include 71 TS and 15 healthy children); and those in the left dendrogram were labeled HA (e.g., 40 healthy and 6 TS adults) or TS adults (e.g., 30 TS adults). The adjusted misclassification rates can be, for example: 5.4% and 21% for the TS children and HC, respectively, and 10% for HA and 16.8% for TS adults. Therefore, the sensitivity and specificity of the procedure can be, for example: 94.6% and 79%, respectively, for classifying a child as either healthy child or as having TS, and were 83.2% and 90%, respectively, for classifying a participant as a TS adult.

As shown in the left column of FIG. 3 (illustration 302), the dorso-anterior and ventro-posterior regions of the right hippocampus can best classify a participant as either a healthy adult or TS adult. Regions in a bright section (302a) are local protrusions, and regions in a dark section (302b) are local indentations, in TS adults compared with healthy adults.

As shown in the right column of FIG. 3 (illustration 304), the regions in right globus pallidus and right hippocampus where the scaling coefficients can differ significantly between TS children and healthy children. The pattern of surface features that can discriminate between the two groups included the dorso-anterior portions of the right globus pallidus, and the dorsal and ventro-posterior portion of the right hippocampus. Regions in a bright section (304a) are local protrusions, and regions in a dark section (304b) are local indentations, in TS children compared with healthy children.

Figure 4:
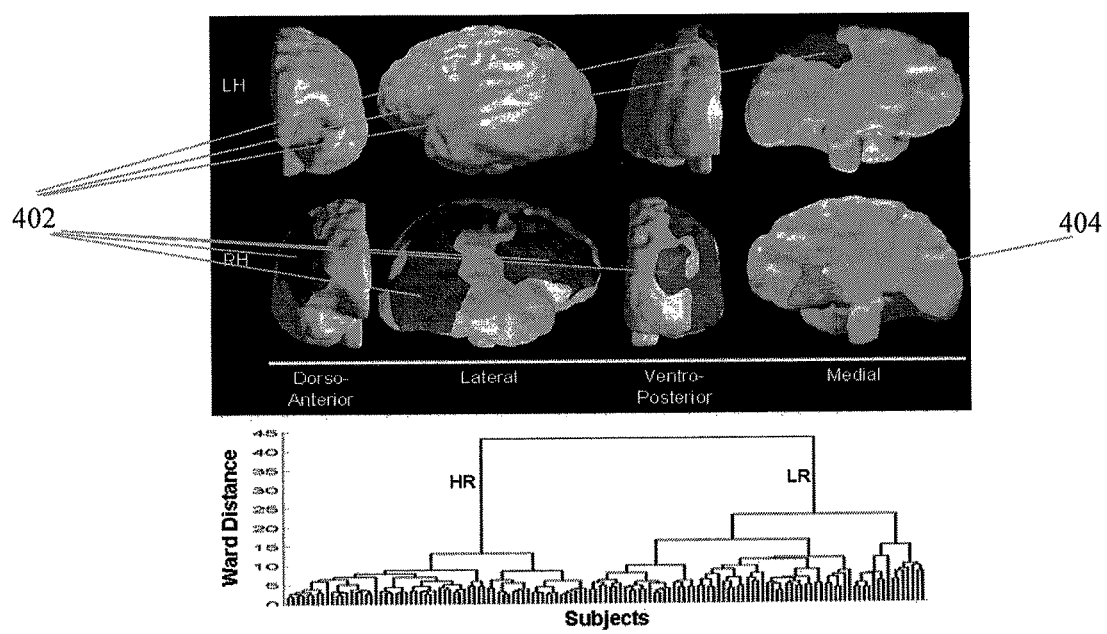
FIG. 4 is an illustration of exemplary classifications of an individuals as having high or low familial risk for MDD using certain exemplary embodiments of the present disclosure.

FIG. 4 shows an illustration of exemplary classifications of an individuals as having high or low familial risk for MDD using certain exemplary embodiments of the present disclosure. The acronyms shown in FIG. 4 are as follows: LH, left hemisphere; RH, right hemisphere. In the exemplary cohort of 66 High Risk (HR) and 65 Low Risk (LR) participants, hierarchical clustering can be applied using Ward's linkages to scaling coefficients computed at Resolution 2 from the local variations in cortical thickness across the right and the left hemispheres. Each group can be assigned a diagnosis using the majority rule, such that a group was labeled HR if the majority of participants in that group belonged to a family with a grandparent who had MDD. Otherwise the group was labeled as LR. Assuming only two groups of participants, the adjusted misclassification rates can be, e.g., 29% for the LR participants and 19% for HR participants. Therefore, the sensitivity and the specificity for classifying an individual as HR can be, e.g., 81% and 71%, respectively. The pattern of cortical thickness that discriminated between the groups included superior regions of the left hemisphere and lateral surface of the right hemisphere. Regions in a bright section (402) are local thickening, and regions in a dark section (404) are local thinning, in HR participants as compared with LR participants. The spatial pattern of variation in cortical thickness in the HR compared with the LR group can be consistent with the pattern previously identified across risk groups in this sample.

Figure 5:
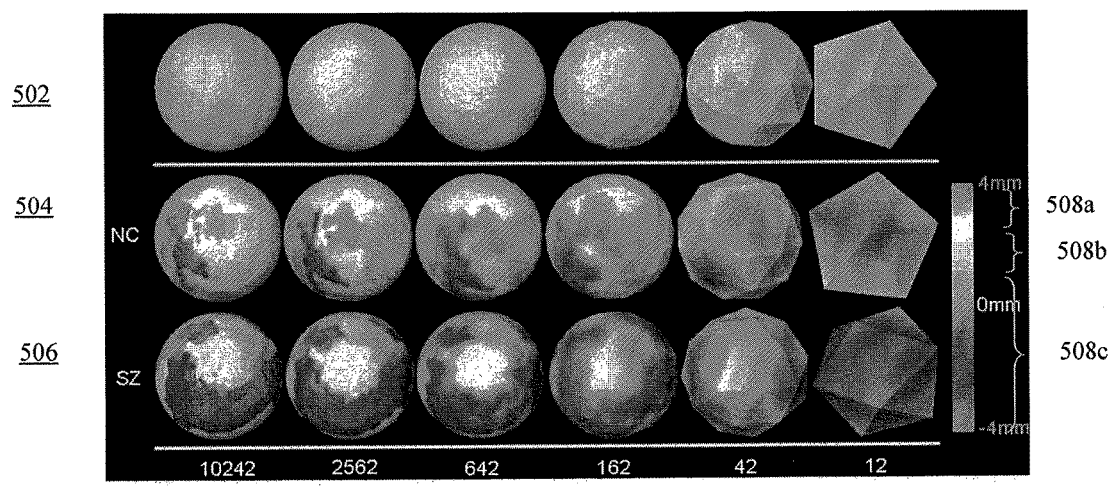
FIG. 5 are a set of images of an exemplary brain with exemplary scaling coefficients at decreasing spatial resolutions according to certain exemplary embodiments of the present disclosure.

FIG. 5 shows illustrations of exemplary scaling coefficients at decreasing spatial resolutions according to certain exemplary embodiments of the present disclosure. The numbers of vertices in the triangulated mesh at each level of resolution are indicated at the bottom of the figure. For example, the meshes with 12 and 162 vertices can correspond to resolutions 0 and 2, respectively, of the spherical wavelet transformation. The top row (502) of FIG. 5 illustrates approximating a unit sphere at decreasing spatial resolutions. The middle row (504) and the bottom row (506) of FIG. 5 illustrates examples of scaling coefficients at decreasing resolutions for local variations in a surface morphological features of the right hippocampus in a representative healthy participant (NC) and a person with Schizophrenia (SZ). The exemplary scaling coefficients are color encoded and displayed at the vertices of sphere at the various resolutions. Protrusions with respect to a template surface are encoded in "Red and Yellow" (508a), and indentations in the surface are encoded in "Violet and Blue" 508b. "Green" 508c indicates no difference in the surface.

The exemplary scaling coefficients can be computed by first using conformal mapping to map local variations in surface morphological features onto a unit sphere and then applying the lifted interpolate transformation to the mapped variations. At the exemplary lowest resolution, e.g., Resolution 0 of the wavelet transformation, scaling coefficients at the 12 vertices of the icosahedron can coarsely approximate the high-resolution variations in local morphological features. Using scaling coefficients at low spatial resolutions for classification can reduce the dimensionality of the feature space.

FIG. 6 shows an illustration of warping a deformed brain to a template brain according to certain exemplary embodiments of the present disclosure. Deformations can be added to copies of the template brain and then the deformed brains can be normalized to the undeformed template. The deformed brains can be spatially normalized using a method that maximizes mutual information in the gray scale values across the images (35) and the coregistered brain can be warped using a method based on fluid dynamics. (36) Because a deformed brain can be identical to the template brain except for the added deformation, the deformation field typically only shows a large spatial deformation in the region of the added deformation.

FIG. 7 shows an illustration of exemplary deformations at a dorsolateral prefrontal cortex (DLPFC) in an exemplary template brain according to certain exemplary embodiments of the present disclosure. As shown in the top row (702) of FIG. 7, in copies of the exemplary template brain, a 15 mm wide protrusion or indentation in the DLPFC can be added by centering the deformation over the midportion of the pars triangular is in the inferior frontal gyrus. The deformed brains can be placed randomly in the coordinate space of the template brain. The deformed brains can be coregistered to the template brain and then the signed Euclidean distances between the surface of the coregistered brain and the surface of the template brain can be computed. The signed Euclidean distances can be color-encoded and displayed on the template brain, and were mapped onto a unit sphere using a conformal mapping. A bright section (706a): protrusion on the surface; and a dark section (706b): indentations on the surface.

As shown in the bottom row (704) of FIG. 7, the exemplary distances on the unit sphere can be transformed by applying spherical wavelet transformation to compute scaling coefficients at decreasing resolutions.

Figure 8:
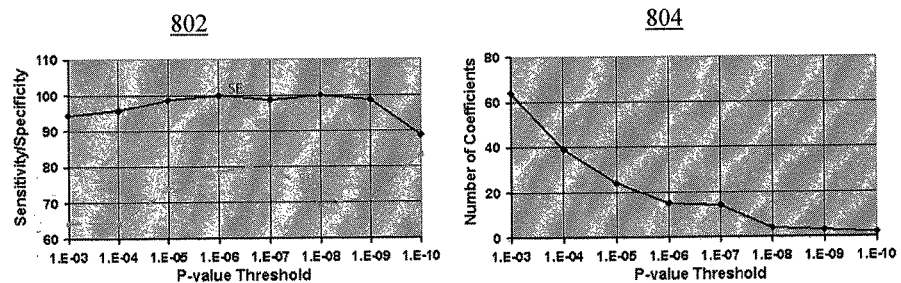
FIG. 8 are a set of graphs of exemplary optimal P-value thresholds for scaling coefficients according to certain exemplary embodiments of the present disclosure.

FIG. 8 shows graphs of exemplary optimal P-value thresholds for scaling coefficients according to certain exemplary embodiments of the present disclosure. The exemplary acronyms shown in FIG. 8 are as follows: SE, sensitivity; SP, specificity. Naturalistic groupings of the brains can be generated using scaling coefficients that can differ significantly with at most a specified P-value between groups of participants in the exemplary cohort. The optimal P-value of the statistical significance can be selected from the plots of sensitivity and specificity, and the number of scaling coefficients, for various P-value thresholds in the exemplary cohort of 42 healthy children (HC) and 71 children with Tourette's Syndrome (TS). The scaling coefficients can be computed for the right and left amygdalae, hippocampi, global pallidus, putamina, caudate nuclei, thalami, and hemisphere surfaces. At each P-value threshold, hierarchical clustering can be applied to the coefficients that differed with at most the specified P-value to generate groupings of the brains. These exemplary groupings can be analyzed using leave-one-out (LOO) cross validation to compute the sensitivity and specificity of the exemplary procedures for classifying an individual as a healthy child or a child with TS. Sensitivity and specificities can be independently computed for various P-value thresholds and the sensitivity (SE, solid line) and specificity (SP, dashed line) can be plotted (Left—802), and the number of coefficients (Right—804) can be plotted, as a function of P-value thresholds. For a P-value threshold<$10^{-7}$, the exemplary procedures can classify an individual with both high sensitivity and high specificity. At this P-value threshold, moreover, the number of coefficients can be sufficiently reduced, thereby reducing the dimensionality of the feature space. Accordingly, a P-value<$10^{-7}$ can be applied as a threshold for classifying an individual among various neuropsychiatric illnesses.

Figure 9:
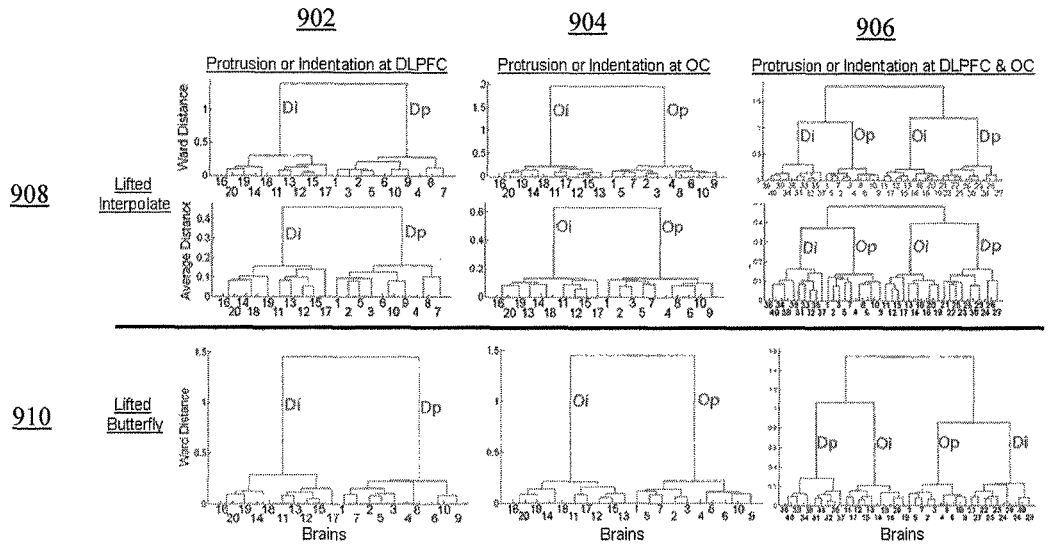
FIG. 9 is an illustration of exemplary identifications of natural groupings of identical brains containing differing known deformations according to certain exemplary embodiments of the present disclosure.

FIG. 9 shows an illustration of exemplary identifications of natural groupings of identical brains containing differing known deformations according to certain exemplary embodiments of the present disclosure. The exemplary acronyms provided in FIG. 9 are as follows: Dp; protrusion in DLPFC; Di; indentation in DLPFC; Op, protrusion in OC; Oi, indentation in OC. As shown in the left column (902) of FIG. 9, brains numbered 1 through 10 contained a protrusion, and brains numbered 11 through 20 contained an indentation, in the DLPFC. As shown in the middle column (904) of FIG. 9, the brains numbered 1 through 10 contained a protrusion, and brains numbered 11 through 20 contained an indentation, in the occipital cortex (OC). As shown in the right column (906) of FIG. 9, the brains numbered 1 through 10 had a protrusion at the OC, the brains numbered 11 to 20 had an indentation at the OC whereas brains numbered 21 through 30 contained a protrusion at the DLPFC and brains numbered 31 through 40 had an indentation at the DLPFC. The deformed brains can be normalized to the template brain to compute the signed Euclidean distances between them at each corresponding point in each of the brains. Those exemplary distances can be then mapped onto a unit sphere using a conformal mapping. Then either the lifted interpolate (top two rows—908) or the lifted butterfly (bottom row—910) can be applied to determine and/or compute the scaling coefficients at Resolution 0. Hierarchical clustering can compute distances between features using either the average linkage or Ward's linkage. Dendrograms in the left and the middle columns 901, 906 can demonstrate that the brains were correctly clustered into two groups, e.g., one with indentations and the other with protrusions at the respective locations. Dendrograms in the third column can show that the brains were correctly clustered into four groups, e.g.: one with protrusions in the OC, another with protrusions in the DLPFC, another one with indentations in the OC, and the last with indentations in the DLPFC. Furthermore, Ward's distances between groups can be larger than the average distances, indicating good separation of groups according to the type of synthetic deformation that was introduced into the data. Ward distances for feature vectors that were generated using lifted interpolate can be generally greater than those generated using lifted butterfly, which can motivate subsequent use of the lifted interpolate wavelet to compute scaling coefficients and use of Ward's linkage to cluster brains into naturalistic groups.

Figure 10:
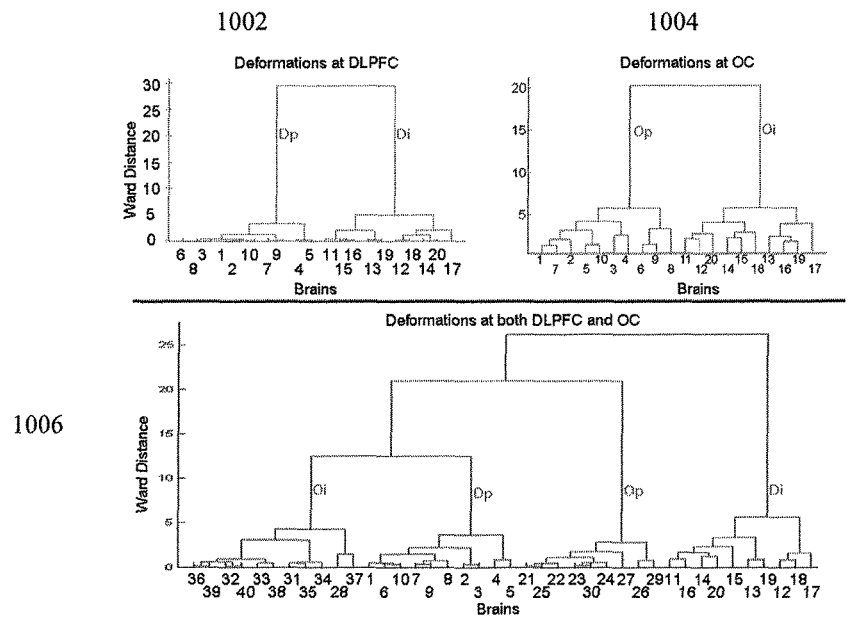
FIG. 10 is an illustration of exemplary identifications of natural groupings of brains with known deformation from differing individuals according to certain exemplary embodiments of the present disclosure.

FIG. 10 shows an illustration of exemplary identifications of natural groupings of brains with known deformation from differing individuals according to certain exemplary embodiments of the present disclosure. The exemplary acronyms shown in FIG. 10 are as follows: Dp; protrusion in DLPFC; Di; indentation in DLPFC; Op, protrusion in OC; Oi, indentation in OC. Deformations can be placed either at the Dorsolateral Prefrontal Cortex (DLPFC) or at the Occipital Cortex (OC) locations in each brain from the 20 differing individuals. As shown in the top row, left column (1002) of FIG. 10, brains 1 through 10 had protrusions and brains 11 through 20 had indentations placed at the DLPFC location. As shown in the top row, right column (1004) of FIG. 10, brains 1 through 10 had protrusions and brains 11 through 20 had indentations placed at the OC location. Because the brains were from different people, they can differ morphologically across the surface in addition to the location of the added deformation. Exemplary variations in surface morphology from the template brain can be analyzed by applying a method for spherical wavelet analysis to compute scaling coefficients at decreasing spatial resolution. The exemplary scaling coefficients that captured variation in the surface at Resolution 2 of the wavelet analysis can be grouped by applying hierarchical clustering that generated correct groupings: brains with indentations and brains with protrusions. As shown in the top row, left column (1002) of FIG. 10, brains 1 through 10 had protrusions, and brains 11 through 20 had indentations, at the DLPFC location. Using the scaling coefficients at Resolution 2 that differed significantly between these groups (e.g., P-value<$10^{-7}$), the dendrogram can show that the brains can be naturally clustered into two groups, e.g.: one with indentations at the DLPFC, and the other with protrusions at the DLPFC. As shown in the top row, right (1004) of FIG. 10, brains 1 through 10 had protrusions, and brains 11 through 20 had indentations, at the OC location. Using a different set of scaling coefficients at Resolution 2 that differed significantly between these groups (e.g., P-value<$10^{-7}$), the dendrogram can show that the data can be naturally clustered into two groups: one with indentations only at the OC, and the other with only protrusions at the OC. As shown in the bottom row (1006) of FIG. 10, brains 1 through 10 had protrusions, and brains 11 through 20 had indentations, at the DLPFC location. Brains 21 through 30 had protrusions, and brains 31 through 40 had indentations, at the OC location. Using scaling coefficients at Resolution 2 at surface vertices that differed significantly between the brains with indentations and protrusions at DLPFC, and the brains with indentations and protrusions at OC, the dendrogram can show that the data can be naturally clustered into 4 groups, e.g.: one with indentations at the DLPFC, another with protrusions at the DLPFC, another with indentations at the OC, and the last with protrusions at the OC location. For example, one brain with protrusion at the OC (Brain 28) can be misclassified by being grouped with brains that had indentations at the OC location.

Figure 11:
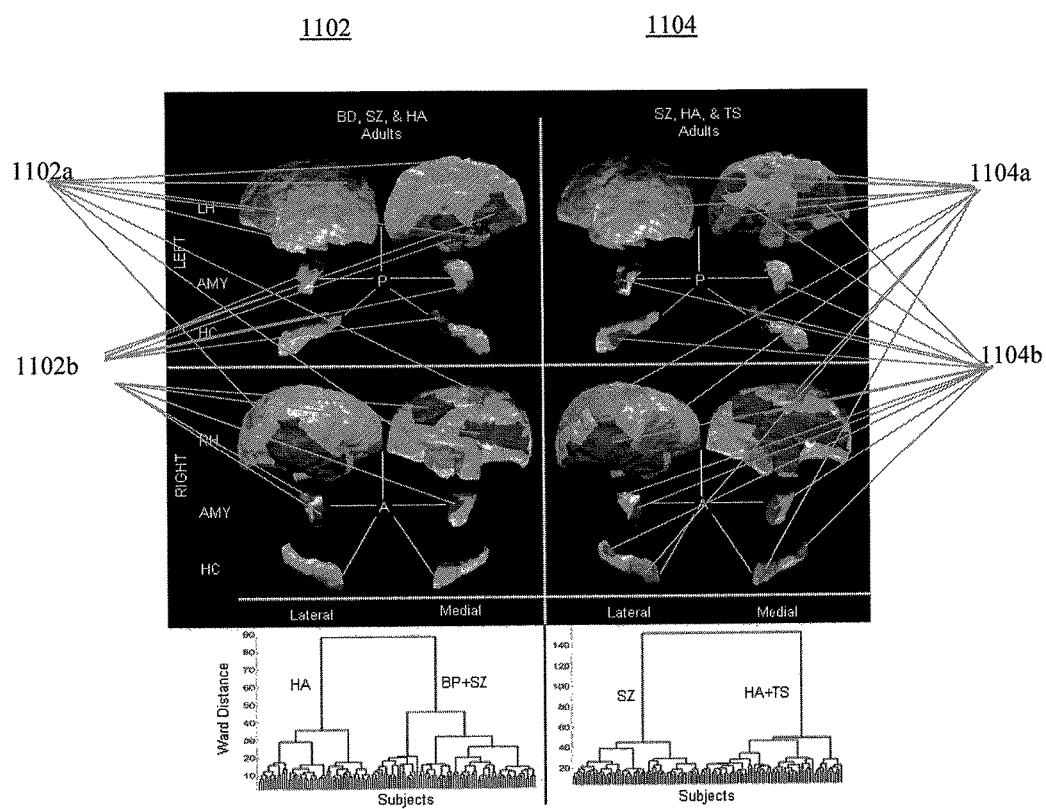
FIG. 11 is an illustration of exemplary three-way classifications of an adult exemplary brain using certain exemplary embodiments of the present disclosure.

FIG. 11 shows an illustration of exemplary three-way classifications of an adult using certain exemplary embodiments of the present disclosure. The exemplary acronyms shown in FIG. 11 are as follows: LH, left hemisphere; RH, right hemisphere; AMY, amygdala; HC, hippocampus; A, anterior; P, posterior. In the exemplary cohort of 40 healthy adults (HA), 26 BD adults, 65 SZ adults, and 36 TS adults, hierarchical clustering can be applied to the scaling coefficients for the left and right amygdalae, hippocampi, and hemisphere surfaces that can be significantly differentiated between (1) both BD and SZ adults from HA (left), and (2) both TS and SZ adults from HA (right). The two largest groups in the left dendrogram can be labeled HA (e.g., this group can include 40 HA) or BD+SZ adults (e.g., this group can include 26 BD adults and 65 SZ adults). The exemplary groups in the right dendrogram can be labeled HA+TS (e.g., this group can include 40 HA and 35 TS adults) or SZ (e.g., this group can include 65 SZ and 1 TS adults). Because the exemplary procedures can perform less than optimally for these 3-way classifications of adults, an iterative two-step procedure for classification of these 3 groups can be used. For example, for classifying an individual as a healthy adult, an adult with BD, or an adult with SZ, first an individual can be classified as belonging to one of two groups, e.g.: (1) a healthy adult, or (2) a patient (e.g., as either an adult with BD or an adult with SZ). The exemplary procedures can classify adults between these two groups with 86% sensitivity and 100% specificity. Second, using a different set of scaling coefficients, the individual can be classified as either an adult with BD or an adult with SZ with high sensitivity and specificity (see, e.g., FIG. 2). Similarly, for classifying an individual as healthy adult, an adults with SZ or an adult with TS, an individual first can be classified between two groups, e.g.: (1) an adult with SZ, and (2) a healthy adult or an adult with TS. The exemplary procedures can classify an adult between these two groups with 99.99% sensitivity and 97.76% specificity. Second, using a different set of scaling coefficients, the individual can be classified as either an adult with TS or a healthy adult (see, e.g., FIG. 3).

As shown on the left column (1102) of FIG. 11, the pattern of the exemplary surface features that can classify an individual as either a healthy adult or a patient (e.g., as either an adults with BD or an adult with SZ) in the first 2-way classification can include: smaller anterior and dorsal portions of the left amygdala, and smaller anterior and lateral portions of the right amygdala; smaller posterior regions of the left hippocampus, and smaller posterior portions of the right hippocampus; larger dorsolateral prefrontal, smaller ventro-medial, and larger parietal portions of the left hemisphere, and larger superior-parietal, larger superior-occipital, smaller temporal, and smaller medial portions of the right hemisphere. Regions in a bright section (1102*a*) are local protrusions, and regions in a dark section (1102*b*) are local indentations, in BD adults or SZ adults compared with healthy adults.

As shown on the right column (1102) of FIG. 11, the pattern of the exemplary surface features that can classify an individual into one of the two groups (either as an adult with SZ, or as a healthy adult or adult with TS) included: anterior and lateral regions of the left and right amygdalae; posterior and lateral regions of the left hippocampus, and anterior and posterior regions of the right hippocampus; anterior, ventral, posterior, medial, and superior regions of the left hemisphere, and medial and lateral regions of the right hemisphere. Regions in a bright section (1104*a*) are local protrusions, and regions in a dark section (1104*b*) are local indentations, in SZ adults compared with healthy adults or adults with TS.

Table 1 provided herein shows an exemplary performance of the exemplary procedures in accordance with the present disclosure using real-world datasets. For example, the exemplary procedure for discriminating the brains of persons with a specific neuropsychiatric disorder from those of healthy persons or persons with other neuropsychiatric disorders can be applied. The misclassification rates can be computed by applying (1) leave-one-out (LOO) analysis to the entire cohort of participants, (2) split-half analysis to 10 pairs of training and test samples, each sample with half the total number of brains in the entire cohort, and (3) LOO analysis to each of the 10 test and 10 training samples used for the split half analyses. The differences in the misclassification rates determined and/or computed in (2) and (3) can be added to the misclassification rates computed for the entire cohort to compute the adjusted misclassification rates. These adjusted rates can be then used to calculate the sensitivity and specificity of the exemplary method for discriminating brains. In addition, the Positive Predictive Value (PPV) that measures the proportion of individuals having the illness (e.g., true positives) among the individuals classified by the procedure as having that illness (e.g., true positives+false positives) can be computed. The PPV can give the likelihood that a person diagnosed with an illness using the exemplary classification procedure actually has the illness and was close to 1 in most of the datasets. The performance of three-way classifications can be poor, however, suggesting an iterative approach with nested two-way classifications for the accurate discrimination of the brains among three clinical conditions. Using the iterative approach for classifying an adult as healthy, with BD, or with SZ, the misclassification rates were 0 for healthy adult, 0.14 for BD adult, and 0.14 for SZ adult. Similarly, for the iterative approach for classifying an adult as healthy, with TS, or with SZ, the misclassification rates can be 0.10 for healthy adult, 0.168 for TS adult, and 0.0245 for SZ adult.

The listed Brain Regions in Table 1 were the regions for which scaling coefficients differed significantly between diagnostic groups at a p-value<$10^{-7}$ and that subsequently were submitted for hierarchical clustering. The acronyms used in Table 1 are as follows: ADHD: Attention Deficit/Hyperactivity Disorder; HC: Healthy children; TS: Tourette Syndrome; SZ: Schizophrenia; BD: bipolar disorder; HA: healthy adults; L: left; R: right; LH: Left Hemisphere; RL, Right Hemisphere; AMY: Amygdala; HC: Hippocampus; GP: Globus Pallidus; PUT: Putamen; TH: Thalamus; CN, Caudate Nucleus; PPV: positive predictive value.

TABLE 1

| Cohort | Demographics | Brain Regions | Misclassification Rates | | | |
|---|---|---|---|---|---|---|
| | | | LOO (Entire Cohort) | Split Half (10 Training & 10 Test Samples) | LOO Split (20 Split Half Samples) | Adjusted (Entire Cohort) |
| ADHD Children | 41 participants, 33 males, 12.6 ± 3.18 years | L&R AMY, L HC. | 0.024 | 0.11 ± 0.11 | 0.07 ± 0.1 | 0.064 |
| Healthy Children | 42 participants, 15 males 10.5 ± 2.43 years | L CN, L&R GP, R PUT, L TH | 0.0952 | 0.16 ± 0.10 | 0.14 ± 0.14 | 0.115 |
| TS Children | 71 participants, 59 males 11.19 ± 2.2 years | L&R AMY, L&R HC. | 0.014 | 0.0105 ± 0.016 | 0.0256 ± 0.021 | 0.0017 |
| ADHD Children | 41 participants, 33 males, 12.6 ± 1.18 years | L CN, L&R GP, L&R PUT, L&R TH | 0 | 0.005 ± 0.0158 | 0 ± 0 | 0.005 |
| SZ Adults | 65 participants, 41 males, 42.16 ± 8.71 years | L&R AMY, L&R HC, | 0 | 0.012 ± 0.022 | 0.0108 ± 0.017 | 0.001 |
| BD Adults | 26 participants, 41 males, 37.66 ± 10.38 years | LH &RH | 0 | 0 ± 0 | 0 ± 0 | 0 |
| BD Adults | 26 participants, 41 males, 37.66 ± 10.38 years | L&R AMY, L HC, | 0 | 0.044 ± 0.048 | 0.044 ± 0.07 | 0 |
| Healthy Adults | 40 participants, 22 males, 32.42 ± 10.7 years | RH | 0.025 | 0.643 ± 0.07 | 0.031 ± 0.033 | 0.036 |
| SZ Adults | 65 participants, 41 males 42.18 ± 8.71 years | L&R AMY, L&R HC, | 0 | 0.003 ± 0.000 | 0 ± 0 | 0.003 |
| TS Adults | 36 participants, 21 males 37.34 ± 10.9 years | LH & RH | 0 | 0 ± 0 | 0 ± 0 | 0 |
| SZ Adults | 65 participants, 41 males 42.18 ± 8.71 years | L&R AMY, L&R HC, | 0.015 | 0.105 ± 0.047 | 0.0525 ± 0.0454 | 0.069 |
| Healthy Adults | 40 participants, 22 males 32.42 ± 10.7 years | LH &RH | 0.025 | 0.04 ± 0.0456 | 0.01 ± 0.02108 | 0.055 |
| TS Adults | 36 participants, 21 males 37.34 ± 10.9 years | R HC | 0.11 | 0.15 ± 0.077 | 0.09 ± 0.09 | 0.166 |
| Healthy Adults | 40 participants, 22 males 32.42 ± 10.7 years | | 0.025 | 0.18 ± 0.193 | 0.10 ± 0.1 | 0.10 |
| TS Children | 71 participants, 59 males, 11.19 ± 2.2 years | R HC, R GP | 0.014 | 0.10 ± 0.177 | 0.09 ± 0.15 | 0.054 |
| Healthy Children | 42 participants, 48 males, 10.5 ± 2.43 years | | 0.19 | 0.29 ± 0.17 | 0.31 ± 0.15 | 0.21 |
| High Risk | 66 participants, 31 males, 33.30 ± 12.90 years | L&R Cortical Thickness | 0.181 | 0.15 ± 0.11 | 0.142 ± 0.11 | 0.19 |
| Low Risk | 65 participants, 30 males, 24.79 ± 13.14 years | | 0.245 | 0.45 ± 0.145 | 0.4 ± 0.143 | 0.29 |
| SZ Adults | 65 participants, 41 males, 42.18 ± 8.71 years | L&R AMY, L&R HC, | 0.0153 0.22 | 0.08 ± 0.14 0.533 ± 0.28 | 0.028 ± 0.045 0.64 ± 0.31 | 0.067 0.11 |
| TS Adults | 36 participants, 21 males 37.34 ± 10.9 years | LH & RH | 0.025 | 0.49 ± 0.31 | 0.035 ± 0.27 | 0.737 |
| Healthy Adults | 40 participants, 22 males, 32.42 ± 10.7 years | | 0.0153 0 | 0.015 ± 0.036 0.011 ± 0.019 | 0.006 ± 0.01 0.01 ± 0.019 | 0.0245 0.001 |
| SZ Adults | 65 participants, 41 males, 42.18 ± 8.71 years | L&R AMY, L&R HC, | 0.015 0.11 | 0.73 ± 0.177 0.28 ± 0.24 | 0.078 ± 0.10 1 ± 0 | 0.80 0.83 |
| BD Adults | 26 participants, 11 males, 37.68 ± 10.36 years | LH & RH | 0 | 0.651 ± 0.057 | 0.007 ± 0.133 | 0.046 |
| Healthy Adults | 40 participants, 22 males, 32.42 ± 10.7 years | | 0.14 0 | 0.167 ± 0.079 0.0121 ± 0.022 | 0.165 ± 0.092 0.011 ± 0.04 | 0.14 0 |

| Cohort | Demographics | Brain Regions | Sensitivity & Specificity (adjusted) | Positive Predictive Value (adjusted) | Comments & FIG. |
|---|---|---|---|---|---|
| ADHD Children | 41 participants, 33 males, 12.6 ± 3.18 years | L&R AMY, L HC. | 93.0% and 85.5% | 0.89 | FIG. 1 |
| Healthy Children | 42 participants, 15 males 10.5 ± 2.43 years | L CN, L&R GP, R PUT, L TH | | | |
| TS Children | 71 participants, 59 males 11.19 ± 2.2 years | L&R AMY, L&R HC. | 99.83% and 99.5% | 0.997 | PPV for predicting TS child (FIG. 1) |
| ADHD Children | 41 participants, 33 males, 12.6 ± 1.18 years | L CN, L&R GP, L&R PUT, L&R TH | | | |

TABLE 1-continued

| Group | Participants | Region | Accuracy | PPV | Notes |
|---|---|---|---|---|---|
| SZ Adults | 65 participants, 41 males, 42.16 ± 8.71 years | L&R AMY, L&R HC, LH &RH | 89.99% and 100% | 1 | PPV for predicting SZ adult (FIG. 2) |
| BD Adults | 26 participants, 41 males, 37.66 ± 10.38 years | | | | |
| BD Adults | 26 participants, 41 males, 37.66 ± 10.38 years | L&R AMY, L HC, RH | 100% and 98.4% | 0.05 | FIG. 2 |
| Healthy Adults | 40 participants, 22 males, 32.42 ± 10.7 years | | | | |
| SZ Adults | 65 participants, 41 males, 42.18 ± 8.71 years | L&R AMY, L&R HC, LH & RH | 99.997% and 100% | 1 | PPV for predicting SZ adult (FIG. 2) |
| TS Adults | 36 participants, 21 males, 37.34 ± 10.9 years | | | | |
| SZ Adults | 65 participants, 41 males, 42.18 ± 8.71 years | L&R AMY, L&R HC, LH &RH | 93.1% 94.5% | 0.963 | FIG. 2 |
| Healthy Adults | 40 participants, 22 males, 32.42 ± 10.7 years | | | | |
| TS Adults | 36 participants, 21 males, 37.34 ± 10.9 years | R HC | 63.2% and 90% | 0.91 | FIG. 3 |
| Healthy Adults | 40 participants, 22 males, 32.42 ± 10.7 years | | | | |
| TS Children | 71 participants, 59 males, 11.19 ± 2.2 years | R HC, R GP | 94.6% and 79% | 0.90 | FIG. 3 |
| Healthy Children | 42 participants, 48 males, 10.5 ± 2.43 years | | | | |
| High Risk | 66 participants, 31 males, 33.30 ± 12.90 years | L&R Cortical Thickness | 91% and 71% | 0.74 | FIG. 4 |
| Low Risk | 65 participants, 30 males, 24.79 ± 13.14 years | | | | |
| SZ Adults | 65 participants, 41 males, 42.18 ± 8.71 years | L&R AMY, L&R HC, LH & RH | | | Classifying an individual among 3 groups: (1) SZ adult, (2) TS adult, or (3) healthy adult (FIG. 37) |
| TS Adults | 36 participants, 21 males, 37.34 ± 10.9 years | | | | |
| Healthy Adults | 40 participants, 22 males, 32.42 ± 10.7 years | | 97.76% and 99.999% | 0.993 | Classifying an individual among two groups: (1) SZ adults, and (2) healthy or TS adult. |
| SZ Adults | 65 participants, 41 males, 42.18 ± 8.71 years | L&R AMY, L&R HC, LH & RH | | | Classifying an individual among 3 groups: (1) SZ adult, (2) BD adult, or (3) healthy adult (FIG. 37) |
| BD Adults | 26 participants, 11 males, 37.68 ± 10.36 years | | | | |
| Healthy Adults | 40 participants, 22 males, 32.42 ± 10.7 years | | 86% and 100% | 1 | Classifying an individual among two groups: (1) SZ adults, or SD adult, and (2) healthy adult. |

Figure 12:
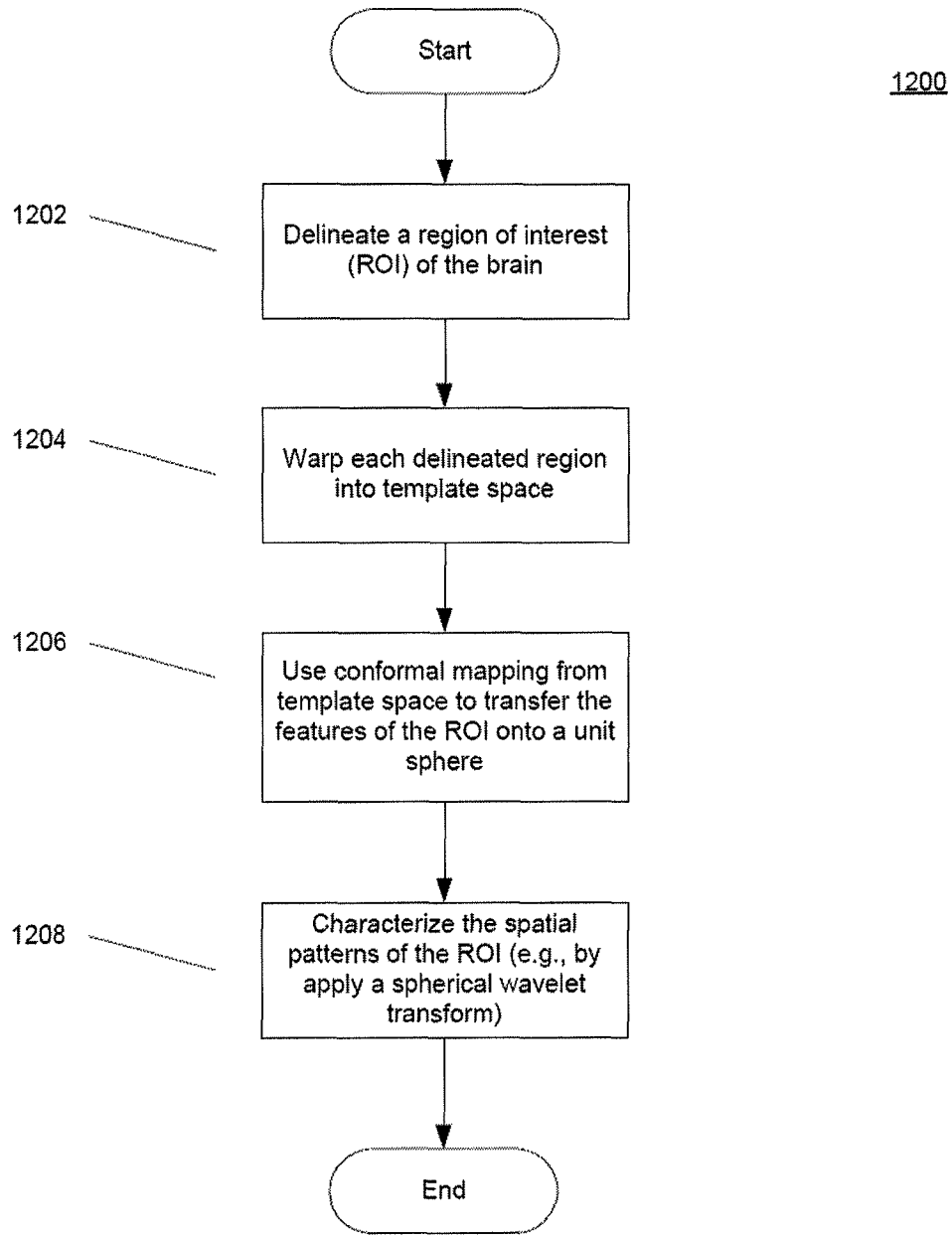
FIG. 12 is a flow diagram of an exemplary method according to certain exemplary embodiments of the present disclosure.

FIG. 12 shows an exemplary method 1200 according to certain exemplary embodiments of the present disclosure, which can be performed, e.g., using a hardware computer processing arrangement). For example, in exemplary method 1200, a region of interest of a brain can be delineated (procedure 1202). The delineated regions can provide surface delineations that are preferably independent of the influences of other regions. Next, the delineated regions can be warped independently into template space unique to each region, free of the influences of the morphological features of other brain regions (procedure 1204). Subsequently, conformal mapping can be used to transfer these local morphological variations from the surface of the template region onto a unit sphere (procedure 1206), to which a spherical wavelet transform can be applied (procedure 1208) to characterize the spatial pattern of this local variation and to reduce the dimensionality of the dataset.

Figure 13:
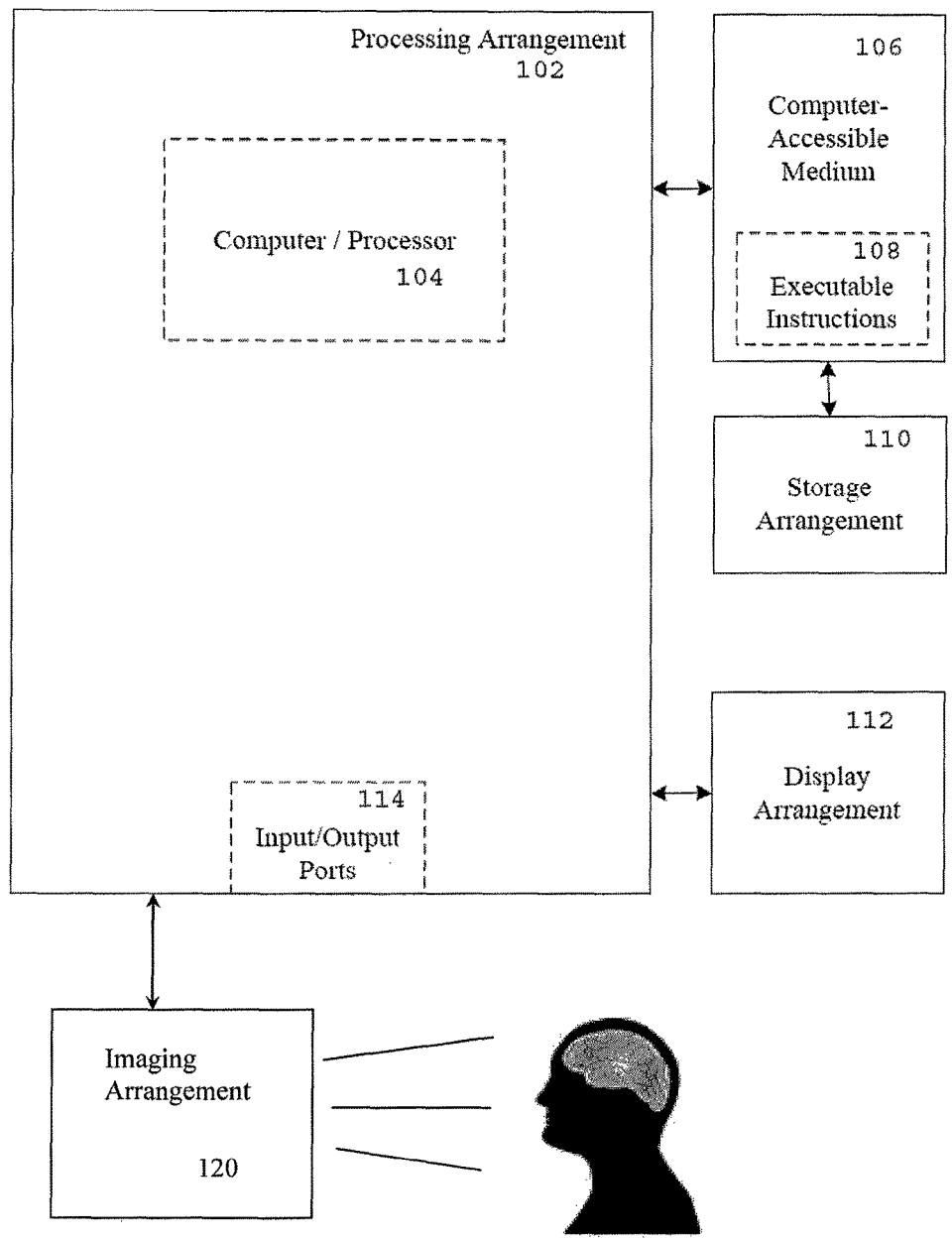
FIG. 13 is a block diagram of an exemplary system in accordance with certain exemplary embodiments of the present disclosure.

FIG. 13 shows an exemplary block diagram of an exemplary embodiment of a system according to the present disclosure. For example, exemplary procedures in accordance with the present disclosure described herein can be performed by an imaging arrangement 120 (e.g., an MRI, CT scan, etc.) and a processing arrangement and/or a computing arrangement 102. Such processing/computing arrangement 102 can be, e.g., entirely or a part of, or include, but not limited to, a computer/processor 104 that can include, e.g., one or more microprocessors, and use instructions stored on a computer-accessible medium (e.g., RAM, ROM, hard drive, or other storage device).

As shown in FIG. 13, e.g., a computer-accessible medium 106 (e.g., as described herein above, a storage device such as a hard disk, floppy disk, memory stick, CD-ROM, RAM, ROM, etc., or a collection thereof) can be provided (e.g., in communication with the processing arrangement 102). The computer-accessible medium 106 can contain executable instructions 108 thereon. In addition or alternatively, a storage arrangement 110 can be provided separately from the computer-accessible medium 106, which can provide the instructions to the processing arrangement 102 so as to configure the processing arrangement to execute certain exemplary procedures, processes and methods, as described herein above, for example.

Further, the exemplary processing arrangement 102 can be provided with or include an input/output arrangement 114, which can include, e.g., a wired network, a wireless network, the internet, an intranet, a data collection probe, a sensor, etc. As shown in FIG. 13, the exemplary processing arrangement 102 can be in communication with an exemplary display arrangement 112, which, according to certain exemplary embodiments of the present disclosure, can be a touch-screen configured for inputting information to the processing arrangement in addition to outputting information from the processing arrangement, for example. Further, the exemplary display 112 and/or a storage arrangement 110 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly.

What is claimed is:

1. A method for diagnosing at least one of (i) an attention deficit hyperactivity disorder, (ii) a bipolar disorder, (iii) a schizophrenia, or (iv) a major depressive disorder for at least one patient, comprising:
   (i) receiving a plurality of structural magnetic resonance (MR) images of a brain of the at least one patient;
   (ii) determining at least one region of interest of the brain of the at least one patient from the structural MR images;
   (iii) mapping the brain in the structural MR images to a template brain;
   (iv) extracting a cortical thickness measure across an entire surface of the brain of the at least one patient based on the template brain;
   (v) determining a plurality of first data points describing a plurality of morphological features for the at least one region of interest based on procedures (iii) and (iv);
   (vi) applying a wavelet transformation (WT) procedure to the first data points in order to generate a plurality of second data points, wherein the second data points are scaling coefficients;
   (vii) identifying a particular spatial pattern of the second data points across the at least one region of interest using the scaling coefficients; and
   (viii) using a computer arrangement, diagnosing the at least one of (i) the attention deficit hyperactivity disorder, (ii) the bipolar disorder, (iii) the schizophrenia, or (iv) the major depressive disorder for the at least one patient by comparing the particular spatial pattern for the at least one patient to at least one known spatial pattern.

2. The method of claim 1, wherein the at least one region of interest includes at least one of (i) a cerebrum, (ii) a cortical mantle, (iii) an amygdala, (iv) a hippocampus, (v) a thalamus, (vi) a caudate nucleus, (vii) a putamen, (viii) a globus pallidus, (ix) a cerebellum, (x) a brainstem, or (xi) white matter of the brain of the at least one patient.

3. The method of claim 1, wherein the determining the first data points further includes:
   correcting a plurality of intensity non-uniformities in the structural MR images,
   orienting the structural MR images of the brain of the at least one patient in a standard Talairach coordinate space,
   isolating the brain from non-brain tissue of the at least one patient in the structural MR images,
   segmenting brain tissue in the structural MR images of the brain as gray or white matter, and
   extracting the morphological features based on the at least one region of interest which includes at least one of (i) at least one subcortical region, (ii) a cerebrum, (iii) a cerebellum, (iv) a brainstem, (v) white matter, or (vi) a cortical mantle of the brain of the at least one patient.

4. The method of claim 3, wherein the extraction of the morphological features comprises computing distances between corresponding points on a plurality of surfaces of the brain in the structural MR images.

5. The method of claim 1, wherein the structural MR images are T1-weighted MR images.

6. The method of claim 1, wherein the identifying of the particular spatial pattern includes obtaining two naturalistic groupings within the second data points.

7. The method of claim 1, wherein the mapping of the brain in the structural MR images to the template brain comprises:
   mapping the brain in the structural MR images so that the brain in the structural MR images is a same size as the template brain, wherein the mapping comprises rotating and scaling the brain in the structural MR images to the template brain such that mutual information between the brain in the structural MR images and the template brain is maximized,
   non-linearly warping the mapped brain such that the mapped brain and the at least one region of interest exactly match a shape of the template brain, wherein the non-linearly warping the mapped brain establishes a correspondence between points on the mapped brain and the template brain;
   mapping the at least one region of interest to a corresponding region of the template brain, and
   non-linearly warping the mapped at least one region of interest to exactly match a shape of the corresponding region of the template brain, wherein the non-linearly warping the mapped at least one region of interest establishes a correspondence between points on the mapped at least one region of interest and the corresponding region of the template brain using the first data points, wherein the first data points include a plurality of further surfaces of the brain of the at least one patient in the structural MR images.

8. The method of claim 7, wherein the generating of the second data points includes applying the WT procedure to each of the plurality of further surfaces of the brain of the at least one patient in the structural MR images.

9. The method of claim 8, wherein the at least one region of interest includes at least one of (i) a cerebrum, (ii) a cortical mantle of the brain, (iii) an amygdala, (iv) a hippocampus, (v) a caudate nucleus, (vi) a putamen, (vii) a globus pallidus, (vii) a thalamus, (viii) a cerebellum, (ix) a brainstem, or (x) white matter.

10. The method of claim 7, further comprising diagnosing the at least one of (i) the attention deficit hyperactivity disorder, (ii) the bipolar disorder, (iii) the schizophrenia, or (iv) the major depressive disorder based on at least one of the scaling coefficients without using any wavelet coefficients.

11. The method of claim 1, further comprising generating a classification procedure by performing procedures (i)-(vii) on a plurality of patients.

12. The method of claim 11, further comprising:
determining the likelihood of the at least one of (i) the attention deficit hyperactivity disorder, (ii) the bipolar disorder, (iii) the schizophrenia, or (iv) the major depressive disorder for at least one further patient by applying the classification procedure to structural MR images obtained from the at least one further patient.

13. The method of claim 1, wherein the second data points include a plurality locations of the morphological features on the entire surface of the brain in the structural MR images.

14. The method of claim 13, wherein the features include protrusions and indentations.

15. The method of claim 1, wherein the WT procedure is a spherical WT procedure.

16. The method of claim 1, wherein the generation of the second data points further includes:
mapping the first data points to a surface of a sphere,
transforming the mapped first data points using the WT procedure to encode the particular spatial pattern, and
performing a linear regression of the second data points using an age and a sex of the at least one patient to remove any variability in the second data points.

17. The method of claim 16, wherein the mapping of the first data points includes conformal mapping that preserves the morphological features using angles between vectors on the template brain and the surface of the sphere.

18. The method of claim 16, wherein the transformation of the mapped first data points includes performing a spherical wavelet analyses on the mapped first data points to generate a plurality of spherical wavelet coefficients and a plurality of spherical scaling coefficients.

19. The method of claim 1, further comprising determining a spatial pattern of abnormality for the at least one of (i) the attention deficit hyperactivity disorder, (ii) the bipolar disorder, (iii) the schizophrenia, or (iv) the major depressive disorder, by optimizing a discriminant ability of the particular spatial pattern.

20. The method of claim 1, wherein the diagnosing of the at least one of (i) the attention deficit hyperactivity disorder, (ii) the bipolar disorder, (iii) the schizophrenia, or (iv) the major depressive disorder, is performed using the computer arrangement, by comparing the particular spatial pattern using a machine learning procedure.

21. The method of claim 20, wherein the diagnosing of the at least one of (i) the attention deficit hyperactivity disorder, (ii) the bipolar disorder, (iii) the schizophrenia, or (iv) the major depressive disorder is performed by the computer arrangement using a hierarchical clustering algorithm applied to a Ward distance of the second data points.

22. The method of claim 21, further comprising, testing a validity and an accuracy of the diagnosis using a split half cross validation procedure.

23. The method of claim 1, wherein the diagnosing of the at least one of (i) the attention deficit hyperactivity disorder, (ii) the bipolar disorder, (iii) the schizophrenia, or (iv) the major depressive disorder is performed by the computer arrangement using the particular spatial pattern by matching the second data points to a plurality of further data points related to a plurality of healthy individuals.

24. The method of claim 23, further comprising correcting the particular spatial pattern for an age and a sex of the at least one patient by performing a linear regression procedure based on a machine learning classification procedure.

25. A non-transitory computer readable medium including instructions thereon for diagnosing at least one of (i) an attention deficit hyperactivity disorder, (ii) a bipolar disorder, (iii) a schizophrenia, or (iv) a major depressive disorder, wherein when a computer arrangement executes the instructions, the computer arrangement is configured to perform procedures comprising :
(i) receiving a plurality of structural magnetic resonance (MR) images of a brain of the at least one patient;
(ii) determining at least one region of interest of the brain of the at least one patient from the structural MR images;
(iii) mapping the brain of the at least one patient in the structural MR images to a template brain;
(iv) extracting a cortical thickness measure across an entire surface of the brain of the at least one patient based on the template brain;
(v) determining a plurality of first data points describing a plurality of morphological features for the at least one region of interest based on procedures (iii) and (iv);
(vi) applying a wavelet transformation (WT) procedure to the first data points in order to generate a plurality of second data points, wherein the second data points are scaling coefficients;
(vii) identifying a particular spatial pattern of the second data points across the at least one region of interest using the scaling coefficients; and
(viii) diagnosing the at least one of (i) the attention deficit hyperactivity disorder, (ii) the bipolar disorder, (iii) the schizophrenia, or (iv) the major depressive disorder for the at least one patient by comparing the particular spatial pattern for the at least one patient to at least one known spatial pattern.

26. The non-transitory computer readable medium of claim 25, wherein the at least one region of interest includes (i) a cerebrum, (ii) a cortical mantel, (iii) an amygdala, (iv) a hippocampus, (v) a thalamus, (vi) a caudate nucleus, (vii) a putamen, (viii) a globus pallidus, (ix) a cerebellum, (x) a brainstem, or (xi) white matter of the brain of the at least one patient.

27. The non-transitory computer readable medium of claim 25, wherein the computer arrangement is further configured to determine the first data points by:
correcting a plurality of intensity non-uniformities in the structural MR images,
orienting the structural MR images of the brain in a standard Talairach coordinate space,
isolating the brain of the at least one patient from non-brain tissue of the at least one patient in the structural MR images,
segmenting brain tissue of the brain in the structural MR images as gray or white matter, and
extracting the morphological features based on the at least one region of interest which includes at least one of (i) at least one subcortical region, (ii) a cerebrum, (iii) a cerebellum, (iv) a brainstem, (v) white matter, or (vi) a cortical mantel of the brain of the at least one patient.

28. The non-transitory computer readable medium of claim 25, wherein the structural MR images are T1-weighted MR images.

29. The non-transitory computer readable medium of claim 25, wherein the identifying of the particular spatial pattern includes obtaining two naturalistic groupings within the second data points.

30. The non-transitory computer readable medium of claim 25, wherein the computer arrangement is configured to map the brain in the structural MR images to the template brain by:
   mapping the brain in the structural MR images so that the brain in the structural MR images is a same size as the template brain, wherein the mapping comprises rotating and scaling the brain in the structural MR images to the template brain such that mutual information between the brain in the structural MR images and the template brain is maximized,
   non-linearly warping the mapped brain such that the mapped brain and the at least one region of interest exactly match a shape of the template brain, wherein the non-linearly warping the mapped brain establishes a correspondence between points on the mapped brain and the template brain;
   mapping the at least one region of interest to a corresponding region of the template brain, and
   non-linearly warping the mapped at least one region of interest to exactly match a shape of the corresponding region of the template brain, wherein the non-linearly warping the mapped at least one region of interest establishes a correspondence between points on the mapped at least one region of interest and the corresponding region of the template brain using the first data points, wherein the first data points include a plurality of further surfaces of the brain in the structural MR images.

31. The non-transitory computer readable medium of claim 30, wherein the computer arrangement is configured to generate the second data points by applying the WT procedure to each of the plurality of further surfaces of the brain in the structural MR images.

32. The non-transitory computer readable medium of claim 25, wherein the computer hardware arrangement is configured to extract the morphological features by computing distances between corresponding points on a plurality of surfaces of the brain in the structural MR images.

33. The non-transitory computer readable medium of claim 25, wherein the at least one region of interest includes at least one of (i) a cerebrum, (ii) a cortical mantle of the brain, (iii) an amygdala, (iv) a hippocampus, (v) a caudate nucleus, (vi) a putamen, (vii) a globus pallidus, (vii) a thalamus, (viii) a cerebellum, (ix) a brainstem, or (x) white matter.

34. An apparatus for diagnosing at least one of (i) an attention deficit hyperactivity disorder, (ii) a bipolar disorder, (iii) a schizophrenia, or (iv) a major depressive disorder for at least one patient, comprising:
   a computer hardware arrangement configured to:
      (i) receive a plurality of structural magnetic resonance (MR) images of a brain of the at least one patient;
      (ii) determine at least one region of interest of the brain of the at least one patient from the structural MR images;
      (iii) map the brain of the at least one patient in the structural MR images to a template brain;
      (iv) extract a cortical thickness measure across an entire surface of the brain of the at least one patient of the at least one patient based on the template brain;
      (v) determine a plurality of first data points describing a plurality of morphological features for the at least one region of interest based on procedures (iii) and (iv);
      (vi) apply a wavelet transformation (WT) procedure to the first data points in order to generate a plurality of second data points, wherein the second data points are scaling coefficients;
      (vii) identify a particular spatial pattern of the second data points across the at least one region of interest using the scaling coefficients; and
      (viii) diagnose the at least one of (i) the attention deficit hyperactivity disorder, (ii) the bipolar disorder, (iii) the schizophrenia, or (iv) the major depressive disorder for the at least one patient by comparing the particular spatial pattern for the at least one patient to at least one known spatial pattern.

35. The apparatus of claim 34, wherein the at least one region of interest includes at least one of (i) a cerebrum, (ii) a cortical mantle, (iii) an amygdala, (iv) a hippocampus, (v) a thalamus, (vi) a caudate nucleus, (vii) a putamen, (viii) a globus pallidus, (ix) a cerebellum, (x) a brainstem, or (xi) white matter of the brain of the at least one patient.

36. The apparatus of claim 34, wherein the computer hardware arrangement is configured to determine the first data points by:
   correcting a plurality of intensity non-uniformities in the structural MR images,
   orienting the structural MR images of the brain at least one patient in a standard Talairach coordinate space,
   isolating the brain of the at least one patient from non-brain tissue of the at least one patient in the structural MR images,
   segmenting brain tissue of the brain in the structural MR images as gray or white matter, and
   extracting the morphological features based on the at least one region of interest which includes at least one of (i) at least one subcortical region, (ii) a cerebrum, (iii) a cerebellum, (iv) a brainstem, (v) white matter, or (vi) a cortical mantle of the brain of the at least one patient.

37. The apparatus of claim 34, wherein the structural MR images are T1-weighted MR images.

38. The apparatus of claim 34, wherein the identifying of the particular spatial pattern includes obtaining two naturalistic groupings within the second data points.

39. The apparatus of claim 34, wherein the computer hardware arrangement is configured to map the brain in the structural MR images to the template brain by:
   mapping the brain in the structural MR images so that the brain in the structural MR images is a same size as the template brain, wherein the mapping comprises rotating and scaling the brain in the structural MR images to the template brain such that mutual information between the brain in the structural MR images and the template brain is maximized,
   non-linearly warping the mapped brain such that the mapped brain and the at least one region of interest exactly match a shape of the template brain, wherein the non-linearly warping the mapped brain establishes a correspondence between points on the mapped brain and the template brain;
   mapping the at least one region of interest to a corresponding region of the template brain, and non-linearly warping the mapped at least one region of interest to exactly match a shape of the corresponding region of the template brain, wherein the non-linearly warping the mapped at least one region of interest establishes a correspondence between points on the mapped at least one region of interest of the brain and the corresponding region of the template brain using the first data points, wherein the first data points include a plurality of further surfaces of the brain of the at least one patient in the structural MR images.

40. The apparatus of claim 39, wherein the computer hardware arrangement is configured to generate the second data points by applying the WT procedure to each of the plurality of further surfaces of the brain in the structural MR images.

41. The apparatus of claim 40, wherein the at least one region of interest includes at least one of (i) a cerebrum, (ii) a cortical mantle of the brain, (iii) an amygdala, (iv) a hippocampus, (v) a caudate nucleus, (vi) a putamen, (vii) a globus pallidus, (vii) a thalamus, (viii) a cerebellum, (ix) a brainstem, or (x) white matter.

42. The apparatus of claim 34, wherein the computer hardware arrangement is configured to extract the morphological features by computing distances between corresponding points on a plurality of surfaces of the brain in the structural MR images.

43. A method for diagnosing at least one of (i) an attention deficit hyperactivity disorder, (ii) a bipolar disorder, (iii) a schizophrenia, or (iv) a major depressive disorder for at least one patient, comprising:
(i) receiving a plurality of structural magnetic resonance (MR) images of a brain of the at least one patient;
(ii) determining at least one region of interest from the structural MR images;
(iii) mapping the brain in the structural MR images to a template brain;
(iv) extracting at least one of (a) a cortical thickness measure across an entire surface of the brain of the at least one patient based on the template brain or (b) a morphology of the at least one region of interest;
(v) determining a plurality of data points describing a plurality of morphological features for the at least one region of interest based on (iii) and (iv);
(vi) generating a plurality of scaling coefficients by reducing a quantity of the data points;
identifying a particular spatial pattern across the at least one region of interest using the scaling coefficients; and
using a computer hardware arrangement, diagnosing the at least one of (i) the attention deficit hyperactivity disorder, (ii) the bipolar disorder, (iii) the schizophrenia, or (iv) the major depressive disorder for the at least one patient by comparing the particular spatial pattern to at least one known spatial pattern.

* * * * *